United States Patent
Hsu et al.

(10) Patent No.: US 11,200,707 B2
(45) Date of Patent: Dec. 14, 2021

(54) METHOD OF MODIFYING A RETINA FUNDUS IMAGE FOR A DEEP LEARNING MODEL

(71) Applicants: National University of Singapore, Singapore (SG); Singapore Health Services Pte Ltd, Singaopre (SG)

(72) Inventors: Wynne Hsu, Singapore (SG); Mong Li Lee, Singapore (SG); Gilbert Lim, Singapore (SG); Tien Yin Wong, Singapore (SG); Shu Wei Daniel Ting, Singapore (SG)

(73) Assignees: National University of Singapore, Singapore (SG); Singapore Health Services Pte Ltd, Singapore (SG)

( * ) Notice: Subject to any disclaimer, the term of this patent is extended or adjusted under 35 U.S.C. 154(b) by 33 days.

(21) Appl. No.: 16/634,442

(22) PCT Filed: Jul. 24, 2018

(86) PCT No.: PCT/SG2018/050363
§ 371 (c)(1),
(2) Date: Jan. 27, 2020

(87) PCT Pub. No.: WO2019/022663
PCT Pub. Date: Jan. 31, 2019

(65) Prior Publication Data
US 2020/0211235 A1 Jul. 2, 2020

(30) Foreign Application Priority Data
Jul. 28, 2017 (SG) .......................... 10201706186V

(51) Int. Cl.
*G06T 11/00* (2006.01)
*A61B 3/00* (2006.01)
(Continued)

(52) U.S. Cl.
CPC .......... *G06T 11/001* (2013.01); *A61B 3/0025* (2013.01); *A61B 3/12* (2013.01);
(Continued)

(58) Field of Classification Search
CPC ...... G06K 9/6271; G06K 9/4628; G06K 9/38; G06K 9/0061; G06K 2209/05; G06N 3/08;
(Continued)

(56) References Cited

U.S. PATENT DOCUMENTS 8,879,813 B1 * 11/2014 Solanki .................... A61B 3/14
382/128
10,019,788 B1 * 7/2018 Kish .................. G06K 9/00369
(Continued)

FOREIGN PATENT DOCUMENTS

| CN | 104463140 A | 3/2015 |
|----|-------------|--------|
| CN | 106725295 A | 5/2017 |
| CN | 105761258 B * | 6/2018 |

OTHER PUBLICATIONS

Youssif et al., "A Comparative Evaluation of Preprocessing Methods for Automatic Detection of Retinal Anatomy", Mar. 24-26, 2007, Proceeding of the Fifth International Conference on Informatics & Systems, pp. 24-30. (Year: 2007).*
(Continued)

*Primary Examiner* — Brenda C Bernardi
(74) *Attorney, Agent, or Firm* — Womble Bond Dickinson (US) LLP; John J. Penny, Jr.

(57) ABSTRACT

A method of modifying a retina fundus image for a deep learning model is disclosed. In a described embodiment, the method includes converting a retina fundus image to a binary image by converting pixels of the retina fundus image to low intensity modified pixels and high intensity modified pixels of the binary image, and determining a first boundary
(Continued)

between the low intensity modified pixels and high intensity modified pixels of the binary image. The method further includes removing outlier boundary values from the first boundary, constructing a second boundary from remaining boundary values, identifying the pixels of the retina fundus image that are within the second boundary, and constructing a modified retina fundus image containing the identified pixels for a deep learning model.

19 Claims, 22 Drawing Sheets

(51) Int. Cl.
*A61B 3/12* (2006.01)
*G06N 3/04* (2006.01)
*G06N 3/08* (2006.01)
*G06T 7/00* (2017.01)
*G06T 11/40* (2006.01)

(52) U.S. Cl.
CPC ............... *G06N 3/04* (2013.01); *G06N 3/08* (2013.01); *G06T 7/0014* (2013.01); *G06T 11/40* (2013.01); *G06T 2207/10024* (2013.01); *G06T 2207/20081* (2013.01); *G06T 2207/30041* (2013.01); *G06T 2210/41* (2013.01)

(58) Field of Classification Search
CPC ......... G06N 3/04; G06T 11/001; G06T 11/40; G06T 7/0014; G06T 2207/30041; G06T 2207/20081; G06T 2207/10024; G06T 2210/41; A61B 3/12; A61B 3/0025
See application file for complete search history.

(56) References Cited

U.S. PATENT DOCUMENTS

| | | | |
|---|---|---|---|
| 2013/0314454 A1* | 11/2013 | Jin | G09G 3/3406 345/690 |
| 2016/0092721 A1 | 3/2016 | Kanagasingam et al. | |
| 2017/0112372 A1* | 4/2017 | Chakravorty | G06K 9/0061 |
| 2018/0220889 A1* | 8/2018 | Dirghangi | A61B 3/12 |
| 2018/0235467 A1* | 8/2018 | Celenk | A61B 3/14 |
| 2019/0191988 A1* | 6/2019 | Gargeya | A61B 5/725 |

OTHER PUBLICATIONS

Goatman et al., "Colour normalisation of retinal images", Oct. 3, 2003, Bio-Medical Physics & Bio-Engineering, pp. 1-7. (Year: 2003).*

Yu et al., "Exudate Detection for Diabetic Retinopahy With COnvolutional Neural Networks", Feb. 2017, 2017 39th Annual International Conference of the IEEE Engineering in Medicine and Biology Society (EMBC), pp. 1744-1747. (Year: 2017).*

Schack et al., "A procedure to locate the eyelid position in noisy videokeratoscopic images", Dec. 13, 2016, EURASIP Journal on Advances in Signal Processing, pp. 1-13. (Year: 2016).*

Sopharak et al., "Machine learning approach to automatic exudate detection in retinal images from diabetic patients", 2010, Journal of Modern Optics, pp. 124-135. (Year: 2010).*

International Search Report and Written Opinion issued in connection with corresponding International Application No. PCT/SG2018/050363 dated Oct. 22, 2018.

Schack, et al., A procedure to locate the eyelid position in noisy videokeratoscopic images, EURASIP Journal on Advances in Signal Processing, Dec. 13, 2016, vol. 2016:136, pp. 1-13.

Sopharak, et al., Machine learning approach to automatic exudate detection in retinal images from diabetic patients, Journal of Modern Optics, Jan. 20, 2010, vol. 57, No. 2, pp. 124-135.

Martinez-Perez, et al., Retinal Blood Vessel Segmentation by Means of Scale-Space Analysis and Region Growing, Medical Image Computing and Computer-Assisted Intervention International Conference, Cambridge, UK, Sep. 19-22, 1999, Sep. 22, 1999, pp. 90-97.

Lim et al., Transformed Representations for Convolutional Neural Networks in Diabetic Retinopathy Screening, Modern Artificial Intelligence for Health Analytics: Papers from the AAAI-14, pp. 21-25.

Cheng et al., Superpixel Classification Based Optic Disc and Optic Cup Segmentation for Glaucoma Screening, IEEE Transactions on Medical Imaging, vol. 32, No. 6., Jun. 2013, pp. 1019-1032.

Quellec, et al., Optimal wavelet transform for the detection of microaneurysms in retina photographs, IEEE Trans Med Imaging, Sep. 27, 2008:1230-41, pp. 1-26.

Lim, et al., Integrated Optic Disc and Cup Segmentation with Deep Learning, Research Gate Conference Paper, Nov. 2015.

Srinivasan, et al., Fully automated detection of diabetic macular edema and dry age-related macular degeneration from optical coherence tomography images, Biomedical Optics Express, Sep. 12, 2014, vol. 5, No. 10.

Gulshan, et al., Development and Validation of a Deep Learning Algorithm for Detection of Diabetic Retinopathy in Retinal Fundus Photographs, JAMA, Nov. 29, 2016, pp. E1-E9.

Gargeya, et al., Automated Identification of Diabetic Retinopathy Using Deep Learning, American Academy of Ophthalmology, vol. 124, No. 7, Jul. 2017, pp. 962-969.

Abramoff, et al., Automated Early Detection og Diabetic Retinopathy, The American Academy of Ophthalmology, vol. 117, No. 6, Jun. 2010, pp. 1147-1154.

* cited by examiner

Table 1: Summary of the training and validation datasets for referable diabetic retinopathy (DR), glaucoma suspect (GS) and age-related macular degeneration (AMD)

| Referable Conditions | Dataset | Countries | Types of cohorts | Ethnicities | Images |
|---|---|---|---|---|---|
| *Referable DR* | | | | | |
| Training dataset | SiDRP 2010-13 | Singapore | Community-based | Chinese, Malay, Indian | 76,370 |
| Primary validation dataset | SiDRP 2014-15 | Singapore | Community-based | Chinese, Malay, Indian | 71,896 |
| External validation datasets | Zhongshan Ophthalmic Center | China | Community-based | Chinese | 15,798 |
| | SiMES | Singapore | Population-based | Malay | 1,936 |
| | SINDI | Singapore | Population-based | Indian | 3,052 |
| | SCES | Singapore | Population-based | Chinese | 4,512 |
| | BES | China | Population-based | Chinese | 1,052 |
| | AFEDS | USA | Population-based | African | 1,968 |
| | DMP[49] | Australia | Clinic-based | Caucasian (white) | 2,302 |
| | Mexican Eye Hospital | Mexico | Clinic-based | Hispanics | 1,172 |
| | CUHK | Hong Kong | Clinic-based | Chinese | 1,254 |
| | HKU | Hong Kong | Clinic-based | Chinese | 7,706 |
| | | | | Total | 189,018 |
| *Referable GS* | | | | | |
| Training dataset | SiDRP 2010-13 | Singapore | Community-based | Chinese, Malay, Indian | 76,108 |
| | SiMES | Singapore | Population-based | Malay | 10,114 |
| | SINDI | Singapore | Population-based | Indian | 10,819 |
| | SCES | Singapore | Population-based | Chinese | 26,731 |
| | SNEC Glaucoma study | Singapore | Clinic-based | Chinese, Malay, Indian | 1,417 |

Figure 11A

| | | | | |
|---|---|---|---|---|
| Primary validation set | SiDRP 2014-15 | Singapore | Community-based | Chinese, Malay, Indian | 71,896 |
| | | | | Total | 197,085 |
| *Referable AMD* | | | | | |
| Training dataset | SiDRP 2010-13 | Singapore | Community-based | Chinese, Malay, Indian | 36,561 |
| | SiMES | Singapore | Population-based | Malay | 8,616 |
| | SINDI | Singapore | Population-based | Indian | 7,447 |
| | SCES | Singapore | Population-based | Chinese | 16,812 |
| | SNEC AMD study | Singapore | Clinic-based | Chinese, Malay, Indian | 2,180 |
| Primary validation dataset | SiDRP 2014-15 | Singapore | Community-based | Chinese, Malay, Indian | 35,948 |
| | | | | Total | 107,564 |
| Total images for DR, GS and AMD training and validation | | | | | 493,667 |

SiDRP 2010-13: Singapore National Diabetic Retinopathy Screening Program 2010 to 2013
SiDRP 2014-15: Singapore National Diabetic Retinopathy Screening Program 2014 to 2015
SiMES: Singapore Malay Eye Study
SINDI: Singapore Indian Eye Study
SCES: Singapore Chinese Eye Study
SNEC: Singapore National Eye Center
BES: Beijing Eye Study
AFEDS: African American Eye Disease Study
DMP: Diabetes Management Project
CUHK: Chinese University of Hong Kong
HKU: University of Hong Kong

Figure 11B

Table 2: Training and validation datasets for diabetic retinopathy (DR)

| Datasets | Number of patients | Number of images | Number of eyes | No DR (N, %) | Mild NPDR (N, %) | Moderate NPDR (N, %) | Severe NPDR (N, %) | PDR (N, %) | DME (N, %) | Ungradable (N, %) |
|---|---|---|---|---|---|---|---|---|---|---|
| *Training* | | | | | | | | | | |
| SiDRP 2010-13 | 13,099 | 76,370 | 38,185 | 33,709 (88.3%) | 3,310 (8.7%) | 597 (1.6%) | 478 (1.3%) | 70 (0.2%) | 2,026 (5.3%) | 21 (0.1%) |
| *Primary Validation* | | | | | | | | | | |
| SiDRP 2014-15* | 14,880 | 71,896 | 35,948 | 33,485 (92.3%) | 1,813 (5.0%) | 455 (1.3%) | 171 (0.5%) | 24 (0.1%) | 320 (0.9%) | 0 (0.0%) |
| *External Validation* | | | | | | | | | | |
| *Community-based* | | | | | | | | | | |
| *Population-based* | | | | | | | | | | |
| 1. Chinese ** (Guangdong, China) | 3,970 | 15,798 | 7,899 | 5,665 (71.7%) | 1,235 (15.6%) | 737 (9.3%) | 0 (0%) | 154 (1.9%) | 0 (0%) | 108 (1.4%) |
| 2. Chinese (Singapore) | 484 | 1,936 | 968 | 759 (78.4%) | 131 (13.5%) | 60 (6.2%) | 1 (0.1%) | 7 (0.7%) | 17 (1.8%) | 10 (1%) |
| 3. Malay (Singapore) | 763 | 3,052 | 1,526 | 1,143 (74.9%) | 215 (14.1%) | 113 (7.4%) | 18 (1.2%) | 9 (0.6%) | 53 (3.5%) | 28 (1.8%) |
| 4. Indian (Singapore) | 1,128 | 4,512 | 2,256 | 1,639 (72.7%) | 422 (18.7%) | 125 (5.5%) | 5 (0.2%) | 17 (0.8%) | 71 (3.1%) | 48 (2.1%) |
| 5. Chinese (Beijing, China) | 263 | 1,052 | 526 | 493 (93.7%) | 4 (0.8%) | 11 (2.1%) | 4 (0.8%) | 0 (0%) | 12 (2.3%) | 2 (0.4%) |
| 6. African Americans (AFEDS) | 492 | 1,968 | 984 | 807 (82.0%) | 50 (5.1%) | 37 (3.8%) | 5 (0.5%) | 16 (1.6%) | 28 (2.85%) | 41 (4.17%) |
| *Clinic-based* | | | | | | | | | | |
| 7. Caucasian (Australia) | 588 | 2,302 | 1,151 | 432 (37.5%) | 121 (10.5%) | 159 (13.8%) | 123 (10.7%) | 191 (16.6%) | 249 (21.6%) | 125 (10.9%) |
| 8. Hispanic (Mexico) | 343 | 1,172 | 586 | 38 (6.5%) | 284 (48.5%) | 192 (32.8%) | 51 (8.7%) | 18 (3.1%) | 223 (38.1%) | 3 (0.5%) |

Figure 12A

| Site | | | | | | | | | | |
|---|---|---|---|---|---|---|---|---|---|---|
| 9. Chinese (CUHK) | 314 | 1,254 | 627 | 224 (35.7%) | 114 (18.2%) | 235 (37.5%) | 43 (6.9%) | 11 (1.8%) | 96 (15.3%) | 0 (0.0%) |
| 10. Chinese*** (HKU) | 1,932 | 7,706 | 3,853 | 1,984 (51.5%) | 1,485 (38.5%) | 155 (4.0%) | 14 (0.4%) | 0 (0%) | 214 (5.55%) | 1 (0.03%) |
| Total | 38,256 | 189,018 | 94,509 | 80,378 (85.0%) | 9,184 (9.72%) | 2,876 (3.04%) | 913 (0.97%) | 517 (0.55%) | 3,309 (3.50%) | 387 (0.41%) |

* 6291 patients in SiDRP 2014-2015 were repeats from SiDRP 2010-2013 and 8,589 were unique patients
** 41 patients had only 1 eye
*** 11 patients had only 1 eye
DR: Diabetic retinopathy; NPDR: Non-proliferative DR; PDR: Proliferative DR; DME: Diabetic macular edema; CUHK: Chinese University of Hong Kong; HKU: The University of Hong Kong

Figure 12B

Table 3: Training set for referable glaucoma suspect (GS) and age-related macular degeneration (AMD)

| Referable Glaucoma Suspect (GS) | Total Images with GS assessment | No. of image with referable GS |
|---|---|---|
| Singapore Diabetic Retinopathy Screening Program (SiDRP) 2010-13 | 76,108 | 120 |
| Singapore Chinese Eye Study | 26,731 | 603 |
| Singapore Malay Eye Study | 10,114 | 333 |
| Singapore Indian Eye Study | 10,819 | 157 |
| Singapore National Eye Center | 1417 | 1,417 |
| Total GS Images | 125,189 | 2,630 |
| Referable Age-related Macular Degeneration (AMD) | Total Images with AMD assessment | No. of images with referable AMD |
| Singapore Diabetic Retinopathy Screening Program (SiDRP) 2010-13 | 36,561 | 19 |
| Singapore National Eye Center | 2,180 | 1,632 |
| Singapore Chinese Eye Study | 16,182 | 43 |
| Singapore Malay Eye Study | 8,616 | 26 |
| Singapore Indian Eye Study | 7,447 | 18 |
| Total AMD Images | 70,986 | 1,738 |

GS: Glaucoma suspect; AMD: age-related macular degeneration
Referable GS – defined as vertical CDR 0.8 and above, local neuro-retinal rim thinning, focal notching, disc haemorrhage, retinal nerve fibre layer defect; Referable AMD – defined as intermediate AMD and/or advanced AMD (geography atrophy and neovascular AMD).

Figure 13

Table 4: Demographics, diabetes history and systemic risk factors of patients attending national Singapore Diabetic Retinopathy Screening Program in 2014 and 2015 (SiDRP 2014-15, primary validation dataset).

| Patients' demographics and vascular risk factors | Mean (SD) / number (%) | % of patient with data |
|---|---|---|
| Total number of retinal images | 71,896 | |
| Total number of eyes | 35,948 | |
| Total number of patients | 14,880 | |
| Age (years) | 60.16 (12.19) | 56.2 |
| Gender, Male | 1151 (54.58) | 56.2 |
| Ethnicity | | |
|   i. Chinese | 1473 (69.84) | 56.2 |
|   ii. Indian | 241 (11.43) | |
|   iii. Malay | 302 (14.32) | |
|   iv. Others | 93 (4.41) | |
| Systemic risk factors | | |
| 1. BMI (kg/m$^2$) | 27.22 (4.99) | 29.7 |
| 2. Diabetes duration (years) | 3.71 (5.51) | 14.7 |
| 3. Systolic blood pressure (mmHg) | 132.05 (17.57) | 43.6 |
| 4. Diastolic blood pressure (mmHg) | 72.77 (10.78) | 43.6 |
| 5. HbA1c (%) | 7.54 (1.88) | 52.1 |
| 6. Total cholesterol (mmol/L) | 4.65 (1.07) | 15.8 |
| 7. HDL cholesterol (mmol/L) | 1.31 (0.35) | 15.8 |
| 8. LDL cholesterol (mmol/L) | 2.61 (0.87) | 15.4 |
| 9. Triglycerides (mmol/L) | 1.68 (2.22) | 15.8 |
| 10. Creatinine (μmol/L) | 75.34 (36.3) | 13.2 |

Figure 16

Table 5: Primary validation dataset showing the area under curve (AUC), sensitivity, specificity, relative true positive fraction (TPF) and relative false positive fraction (FPF) of deep learning system (DLS) versus trained professional graders in patients with diabetes attended national Singapore diabetic retinopathy screening program (SiDRP 2014-15), , with reference to retinal specialist's grading.

| | Diagnostic Performance for Referable DR and VTDR | | | | |
|---|---|---|---|---|---|
| | Area under curve (95% CI)+ | Sensitivity (95% CI)^ | Specificity (95% CI)^ | TPF difference*** (95% CI), p-value | FPF difference*** (95% CI), p-value |
| *1. Referable DR\** | | | | | |
| i. DLS | 0.936 (0.925, 0.943) | 90.49 (87.25, 92.97) | 91.56 (91.01, 92.23) | -0.70 (-4.24, 2.85), 0.68 | 7.44 (7.15, 7.72), <0.0001 |
| ii. Graders | 0.992 (0.987, 0.996) | 91.18 (87.97, 93.60) | 99.34 (99.24, 99.42) | [Reference] | [Reference] |
| *2. VTDR\*\** | | | | | |
| i. DLS | 0.958 (0.956, 0.961) | 100.0 (94.13, 100.00)# | 91.07 (90.70, 91.42) | 11.48 (1.84, 21.11), <0.01 | 8.57 (8.27, 8.86), <0.0001 |
| ii. Graders | 0.997 (0.996, 0.998) | 88.52 (75.30, 95.13) | 99.63 (99.55, 99.70) | [Reference] | [Reference] |

Eyes were the units of analysis (n=35,948)
DR: Diabetic retinopathy; VTDR: Vision-threatening diabetic retinopathy
^ Asymptotic 95% confidence interval was computed for the logit of each proportion and using the cluster sandwich estimator of standard error to account for possible dependency of eyes within each individual
Exact Clopper-Pearson left-sided 97.5% confidence interval was calculated due to estimate being at the boundary
+ Cluster-bootstrap biased-corrected 95% confidence interval was computed for each AUC, where individual patients were the bootstrap sampling clusters
\* Referable DR was defined as moderate non-proliferative DR (NPDR), severe (NPDR), proliferative DR (PDR) and 'un-gradable' eye
\*\* VTDR was defined as severe NPDR and PDR
\*\*\* Absolute difference in true positive fraction (TPF) and false positive fraction (FPF) between automated DR screening program and trained graders; TPF is equivalent to sensitivity; FPF is equivalent to 1-specificity
The DME detection rate amongst referable DR eyes = 98.17 (94.37 to 99.42)

Figure 17

Table 6: The area under curve (AUC), sensitivity, specificity, area under curve, relative true positive fraction (TPF) and relative false positive fraction (FPF) of deep learning system (DLS) versus trained professional graders, with reference to retinal specialist's grading in unique SiDRP 14-15 patients.

| | Area under curve (95% CI)+ | Sensitivity (95% CI)^ | Specificity (95% CI)^ | TPF difference*** (95% CI), p-value | FPF difference*** (95% CI), p-value |
|---|---|---|---|---|---|
| 1. Referable DR* | | | | | |
| i. DLS | 0.879 (0.864, 0.893) | 89.56 (85.51, 92.58) | 83.49 (82.68, 84.27) | 4.71 (-0.16, 9.59), 0.04 | 15.06 (14.25, 15.87), <0.0001 |
| ii. Graders | 0.917 (0.897-0.937) | 84.84 (81.28, 88.51) | 98.55 (98.27, 98.79) | [Reference] | [Reference] |
| 2. VTDR** | | | | | |
| i. DLS | 0.908 (0.900, 0.915) | 100.0 (90.97 to 100.0)# | 81.40 (80.57, 82.22) | 10.26 (-0.18, 22.34), 0.04 | 17.68 (16.85, 18.50), <0.0001 |
| ii. Graders | 0.944 (0.896-0.992) | 89.74 (74.77, 96.27) | 99.09 (98.86, 99.27) | [Reference] | [Reference] |

Patients were the units of analysis (n=8,589)
DR: Diabetic retinopathy; VTDR: Vision-threatening diabetic retinopathy
^ Asymptotic 95% confidence interval was computed for the logit of each proportion
Exact Clopper-Pearson left-sided 97.5% confidence interval was calculated due to estimate being at the boundary
+ Asymptotic 95% confidence interval was computed for each AUC
* Referable DR was defined as one of the eyes with at least moderate non-proliferative DR (NPDR), severe (NPDR), proliferative DR (PDR) or 'un-gradable'
** VTDR was defined as severe NPDR and PDR
*** Absolute difference in true positive fraction (TPF) and false positive fraction (FPF) between automated DR screening program and trained graders; TPF is equivalent to sensitivity; FPF is equivalent to 1-specificity
Eyes rated 'un-gradable' are treated as referable status
In patients with information in one eye missing, the other eye is used solely to determine referable status
The DME detection rate amongst referable DR eyes = 97.71 (93.04 to 99.27)

Figure 18

Table 7: External validation datasets showing the area under curve (AUC), sensitivity, specificity, positive predictive value and negative predictive value of deep learning system (DLS) in detecting referable diabetic retinopathy (DR) and detection rate of vision-threatening DR (VTDR) among populations with diabetes, with reference to trained professional graders

| Dataset/Ethnicity | City/Country | Diagnostic Performance for Referable DR | | | | | VTDR** |
|---|---|---|---|---|---|---|---|
| | | Area under curve (95% CI)+ | Sensitivity (95% CI)^ | Specificity (95% CI)^ | Positive predictive value (95% CI)^ | Negative predictive value (95% CI)^ | Detection Rate, % |
| *i) Community-based* | | | | | | | |
| 1. Chinese | Guangdong, China | 0.949 (0.943, 0.955) | 98.65 (97.66, 99.3) | 81.62 (80.69, 82.53) | 40.94 (38.85, 43.06) | 99.79 (99.63, 99.89) | 100.0 |
| *ii) Population-based* | | | | | | | |
| 2. Chinese | Singapore | 0.919 (0.900, 0.942) | 100.00 (92.52, 100.00)# | 76.29 (72.69, 79.55) | 24.37 (18.61, 31.23) | 100.00 (99.46, 100.00)# | 100.0 |
| 3. Malay | Singapore | 0.889 (0.863, 0.908) | 97.14 (92.52, 98.94) | 82.03 (79.37, 84.42) | 35.79 (29.91, 42.13) | 99.64 (99.05, 99.87) | 92.6 |
| 4. Indian | Singapore | 0.917 (0.899, 0.933) | 99.32 (95.14, 99.91) | 73.27 (70.86, 75.54) | 20.95 (17.32, 25.11) | 99.93 (99.53, 99.99) | 100.0 |
| 5. Chinese | Beijing, China | 0.929 (0.903, 0.955) | 94.44 (72.71, 99.86) | 88.51 (85.41, 91.16) | 22.67 (13.79, 33.79) | 99.78 (98.76, 99.99) | 100.0 |
| 6. African Americans | Los Angeles, USA | 0.980 (0.971, 0.989) | 98.8 (93.47, 99.97) | 86.51 (84.05, 88.72) | 41.41 (34.48, 48.61) | 99.87 (99.25, 100) | 97.0 |
| *iii) Clinic-based* | | | | | | | |

Figure 19A

| | | | | | |
|---|---|---|---|---|---|
| 7. Caucasian | Melbourne, Australia | 0.983 (0.972, 0.991) | 98.94 (97.47, 99.56) | 92.22 (89.52, 94.27) | 100.0 |
| 8. Hispanic | Mexico | 0.950 (0.934, 0.966) | 91.76 (88.44, 94.37) | 84.78 (80.39, 88.53) | 91.59 (88.68, 93.85) |
| | | | | 87.21 | 99.03 (97.68, 99.60) |
| 9. Chinese | Hong Kong | 0.948 (0.921, 0.972) | 99.31 (97.25, 99.83) | 83.14 (77.93, 87.31) | 90.1 |
| | | | | 83.43 (78.24, 87.58) | 98.8 |
| 10. Chinese | Hong Kong | 0.964 (0.958, 0.97) | 100 (98.95, 100) # | 81.32 (79.99, 82.6) | 99.29 (97.17, 99.83) |
| | | | | 34.93 (31.98, 37.96) | 98.2 |
| | | | | | 100 |
| | | | | | 100 (99.87, 100) # |

∧ Asymptotic 95% confidence interval was computed for the logit of each proportion and using the cluster sandwich estimator of standard error to account for possible dependency of eyes within each individual \# Exact Clopper-Pearson left-sided 97.5% confidence interval was calculated due to estimate being at the boundary + Cluster-bootstrap biased-corrected 95% confidence interval was computed for each AUC, where individual patients were the bootstrap sampling clusters

* Referable DR was defined as moderate non-proliferative DR (NPDR), severe (NPDR), proliferative DR (PDR) and un-gradable images

** VTDR was defined as severe NPDR and PDR. The detection rate is the proportion of VTDR detected using the same threshold set for referable DR. The AUC for Dataset 1 to 10 are 0.926 (dataset 1), 0.959 (dataset 2), 0.875 (dataset 3), 0.912 (dataset 4), 0.952 (dataset 5), 0.936 (dataset 6), 0.822 (dataset 7), 0.822 (dataset 8), 0.906 (dataset 9) and 0.958 (dataset 10), respectively.

Figure 19B

The receivers' operating curve (ROC) and area under curve (AUC) of deep learning system (DLS) for detection of:

(A) Referable diabetic retinopathy (DR) and vision-threatening diabetic retinopathy (VTDR) in the national Singapore diabetic retinopathy screening program (SiDRP 2014-15);
(B) Referable DR stratified by age, gender and glycemic control in SiDRP 2014-15
(C) Referable DR and VTDR in 10 populations of different ethnicities – Chinese (Guangdong, China), Chinese (Singapore), Malay (Singapore), Indian (Singapore), Chinese (Beijing, China), African American (Los Angeles, USA), Caucasian (Melbourne, Australia), Hispanic (Mexico), Chinese (Hong Kong) and Chinese (Hong Kong).

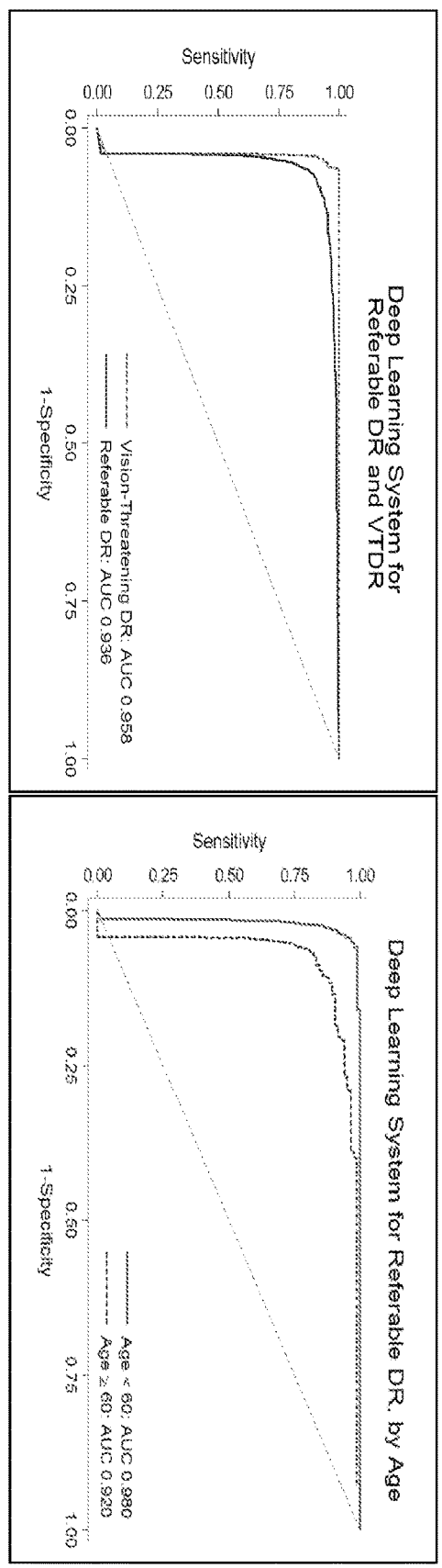

Graph A

Graph B1

Figure 20A

Eyes are the units of analysis
Cluster-bootstrap biased-corrected 95% confidence interval (CI) was computed for each AUC, where individual patients were the bootstrap sampling clusters
Referable diabetic retinopathy (DR): Defined as moderate non-proliferative DR (NPDR), severe NPDR, proliferative DR and diabetic macular oedema
Vision-threatening diabetic retinopathy: Defined as severe NPDR and PDR
A: SiDRP 2014-15 cohort (with reference to a retinal specialist)
i. Referable DR: 0.936 (0.925, 0.943); VTDR: 0.958 (0.956, 0.961)
B: SiDRP 2014-15 cohort stratified by age, gender and HbA1c (with reference to a retinal specialist)
i. Age <60 years: 0.980 (0.975, 0.984); Age ≥ 60: 0.920 (0.889, 0.940)
ii. Male: 0.952 (0.925, 0.963); Female: 0.948 (0.9333, 0.956); 3)
iii. HbA1c <8%: 0.938 (0.892, 0.958); HbA1c ≥ 8% 0.954 (0.942, 0.964)
C: Referable DR and VTDR in 10 populations with different ethnicities (with reference to professional graders)
i. Referable DR – Chinese (Guangdong, China): 0.949 (0.943,0.955); Chinese (Singapore): 0.919 (0.900, 0.942); Malay (Singapore): 0.889 (0.863, 0.908); Indian (Singapore): 0.917 (0.899, 0.933); Chinese (Beijing, China): 0.929 (0.903,0.955); African American (USA): 0.980 (0.971, 0.989); Caucasian (Melbourne, Australia): 0.983 (0.972, 0.991); Hispanic (Mexico): 0.950 (0.934, 0.956); Chinese (Hong Kong): 0.948 (0.921, 0.972); Chinese (Hong Kong): 0.964 (0.958, 0.970)
ii. VTDR - Chinese (Guangdong, China): 0.926 (0.910, 0.943); Chinese (Singapore): 0.959 (0.943, 0.974); Malay (Singapore): 0.875 (0.845,0.894); Indian (Singapore): 0.912 (0.855,0.936); Chinese (Beijing, China): 0.914 (0.874,0.953); African American (USA): 0.952 (0.931, 0.974); Caucasian (Melbourne, Australia): 0.936 (0.915, 0.950); Hispanic (Mexico): 0.822 (0.766, 0.864); Chinese (Hong Kong): 0.906 (0.858, 0.938) and; Chinese (Hong Kong): 0.958 (0.940, 0.976).

Figure 20C

Table 8: Primary validation dataset showing the area under curve (AUC), sensitivity, specificity, positive predictive value and negative predictive value of deep learning system (DLS) in detecting referable glaucoma suspect (GS) and referable AMD (AMD) among patients with diabetes attending national Singapore diabetic retinopathy screening program (SiDRP 2014-15), with reference to a retinal and glaucoma specialists.

| | Diagnostic Performance for Referable GS and Referable AMD | | | | |
|---|---|---|---|---|---|
| | Area under curve (95% CI)[+] | Sensitivity (95% CI)[^] | Specificity (95% CI)[^] | Positive predictive value (95% CI)[^] | Negative predictive value (95% CI)[^] |
| Referable GS | 0.942 (0.929,0.954) | 96.40 (81.65,99.91) | 87.17 (86.81,87.52) | 0.61 (0.4,0.88) | 100 (99.98,100)[#] |
| Referable AMD | 0.931 (0.928,0.935) | 93.17 (91.14,99.75) | 88.65 (88.29,89.01) | 17.46 (16.3,18.7) | 99.8 (99.74,100)[#] |

GS: glaucoma suspect; AMD: age-related macular degeneration
Referable GS: defined as vertical cup/disc diameter ratio of ≥0.8, focal thinning or notching of the neuroretinal rim, optic disc haemorrhages, or localized retinal nerve fibre layer defects.
Referable AMD: defined as the presence of intermediate AMD (numerous intermediate drusens, 1 large drusen >125um) and/or advanced AMD - geographic atrophy (GA) or neovascular AMD, using the age-related eye disease study (AREDS) grading system.[52]

Repeats from SIDRP 14-15 were excluded from the analysis
[^] Asymptotic 95% confidence interval was computed for the logit of each proportion and using the cluster sandwich estimator of standard error to account for possible dependency of eyes within each individual
[#] Exact Clopper-Pearson left-sided 97.5% confidence interval was calculated due to estimate being at the boundary
[+] Cluster-bootstrap biased-corrected 95% confidence interval was computed for each AUC, where individual patients were the bootstrap sampling clusters

Figure 21

METHOD OF MODIFYING A RETINA FUNDUS IMAGE FOR A DEEP LEARNING MODEL

The present application claims priority under 35 U.S.C. § 119 to Singaporean Application No. 10201706186V filed on Jul. 28, 2017, and under 35 U.S.C. § 365 to International Application No. PCT/SG2018/050363 filed on Jul. 24, 2018. The entire contents of these applications are incorporated herein by reference in their entirety.

TECHNICAL FIELD

The present disclosure relates to image processing for deep learning techniques, and more particularly but not exclusively, to a method of modifying a retina fundus image for a deep learning model.

BACKGROUND

Diabetic retinopathy (DR) is a leading cause of vision loss globally. Screening for DR, coupled with timely referral and treatment is a universally accepted strategy for the prevention of visual impairment. Currently, clinical ophthalmoscopy or evaluation of retinal photographs for DR by human assessors are the most commonly used DR screening methods. However, such DR screening programs are challenged by implementation issues, availability and training of assessors and long-term financial sustainability. With increasing diabetes prevalence globally, there is a need for sustainable cost-effective DR screening programs.

Deep learning system (DLS) has been proposed as an option for large-scale screening of DR by analyzing retinal images. DLS utilizes artificial intelligence and representation-learning methods to process natural raw data, recognizing intricate structures in high-dimensional information. In contrast to traditional pattern recognition type software to detect specific images, patterns and lesions, DLS uses large datasets to enable mining, extraction and machine learning of meaningful patterns or features.

The performance of DLS partly depends on the datasets used to train and/or validate the model. For example, two previous DLS studies were shown to have substantial potential for DR screening, demonstrating high sensitivity and specificity (>90%) in detecting referable DR from retinal photographs. However, the performance indices used were based on high quality retinal images retrieved from two publicly available databases, and largely confined to a single ethnic group.

In "real-world" DR screening programs, there may be considerable variability to the retinal images captured for screening. For example, different camera models may be used resulting in image discrepancies. The capture standards may also vary among screening centers which result in retinal images having varying qualities (e.g. poor pupil dilation, poor contrast/focus). Patients may also be of different ethnicities resulting in the captured retinal images having different fundi pigmentations. These variables will have an effect on the performance of a DLS trained on high quality retinal images with low variability. For the performance of the DLS in a test setting to be translated to the "real-world", the DLS should be trained and validated using "real-world" DR screening programs where the retinal images used for training are affected by "real-world" variables.

Furthermore, in any screening programs for DR, it is desirous that the detection of incidental but common vision-threatening condition such as glaucoma (GS) and age-related macular degeneration (AMD) is incorporated. This further widens the variability of retinal images to be incorporated into the training dataset for the DLS.

Therefore, it is desirable to provide a way for DLS to be trained by a wide variety of retinal images in order to address the problems mentioned in existing prior art and/or to provide the public with a useful choice.

SUMMARY

Various aspects of the present disclosure will now be described in order to provide a general overview of the present disclosure. These, by no means, delineate the scope of the invention.

According to a first aspect, there is provided a method of modifying a retina fundus image for a deep learning model. The method includes converting a retina fundus image to a binary image by converting pixels of the retina fundus image to low intensity modified pixels and high intensity modified pixels of the binary image, and determining a first boundary between the low intensity modified pixels and high intensity modified pixels of the binary image. The method further includes removing outlier boundary values from the first boundary, constructing a second boundary from remaining boundary values, identifying the pixels of the retina fundus image that are within the second boundary, and constructing a modified retina fundus image comprising the identified pixels for the deep learning model.

The described embodiment is used to standardize captured retinal fundus images before screening by a trained DLS. Furthermore, the described embodiment allows large scale usage of "real-world" retina fundus images captured from screening programs for training of a deep learning model. The trained model or DLS has translational impact in terms of its performance in the 'real-world".

The retina fundus image may be a grayscale image.

The method may further include converting a coloured retina fundus image to the grayscale retina fundus image using green channel values prior to converting the retina fundus image to the binary image.

Converting the retina fundus image to the binary image may include classifying the pixels of the retina fundus image with corresponding intensity values below a predefined intensity threshold as the low intensity modified pixels and the pixels of the retina fundus image with corresponding intensity values above the predefined intensity threshold as the high intensity modified pixels.

Each of the low intensity modified pixels may have an intensity value of '0' and each of the high intensity modified pixels may have an intensity value of '255'.

Converting the retina fundus image to the binary image may be performed using two-class Otsu algorithm.

The method may further include capping pixel intensity of the retina fundus image at a pre-set maximum intensity, prior to converting the retina fundus image to the binary image.

The maximum intensity may be pre-set to '50'.

The method may further include defining the binary image in terms of polar coordinates, prior to determining the first boundary.

The high intensity modified pixels may be located within the first boundary and the low intensity modified pixels may be located outside the first boundary.

Determining the first boundary may include defining the first boundary in terms of boundary values in polar coordinates.

Removing outlier boundary values may include computing a mean radial value from the boundary values and removing the boundary values that have radial values that are undefined or deviate from the mean radial value.

The boundary values which deviate from the mean radial value by more than 10 units may be removed.

The method may further include applying quadratic regression to the remaining boundary values to construct the second boundary.

The method may further include defining the second boundary in Cartesian coordinates, prior to identifying the pixels of the retina fundus image that are within the second boundary.

Constructing the modified retina fundus image may include copying the identified pixels into the second boundary, and filling unoccupied pixels within the second boundary with a background of the modified retina fundus image.

The method may further include rescaling the modified retina fundus image to 512×512 pixels.

It should be appreciated that the method may be implemented by a specially configured computer or computing system. This then forms a second aspect, in which there is provided a non-transient computer readable medium storing executable instructions when executed by a processor causes the processor to perform the method of the first aspect.

The method has many uses and in one particular application, according to a third aspect, there is provided a deep learning system for screening eye diseases in which the deep learning system includes a dataset trained by the retina fundus image of the method of the first aspect.

BRIEF DESCRIPTION OF FIGURES

An exemplary embodiment will be described with reference to the accompanying drawings in which:

FIG. 11A-11B is a table presenting data on the number of retina fundus images (to be modified using method 100 of FIG. 1) in each of the training and validation datasets for DR, GS and AMD;

FIGS. 12A-12B is a table presenting further data on the DR training and validation datasets of FIGS. 11A-11B;

FIG. 13 is a table presenting further data on the GS and AMD training datasets of FIGS. 11A-11B;

FIG. 16 is a table presenting data on the overall demographics, diabetes history and systemic risk factors of patients in the primary validation dataset (SiDRP 2014-15) presented in FIGS. 11A and 12A;

FIG. 17 is a table presenting data on the diagnostic performance of the DLS for referable DR and VTDR compared to professional graders, evaluated on the primary validation dataset (SiDRP 2014-15) presented in FIGS. 11A and 12A;

FIG. 18 is a table presenting data on the diagnostic performance of the DLS for referable DR and VTDR compared to professional graders, evaluated on unique patients in the primary validation dataset (SiDRP 2014-15) presented in FIGS. 11A and 12A;

FIG. 19A-19B is a table presenting data on the diagnostic performance of the DLS for referable DR and VTDR compared to professional graders, evaluated on the external validation datasets presented in FIGS. 11A, 12A and 12B;

FIGS. 20A-20C depict graphs built on the performance data of FIG. 17; and FIG. 19A-19B; and FIG. 21 is a table presenting data on the diagnostic performance of the DLS for referable GS and AMD compared to professional graders, evaluated on the primary validation dataset (SiDRP 2014-15) presented in FIG. 11B.

DETAILED DESCRIPTION

One or more embodiments of the present disclosure will now be described with reference to the figures. The use of the term "an embodiment" in various parts of the specification does not necessarily refer to the same embodiment. Furthermore, features described in one embodiment may not be present in other embodiments, nor should they be understood as being precluded from other embodiments merely from the absence of the features from those embodiments. Various features described may be present in some embodiments and not in others.

Additionally, figures are there to aid in the description of the particular embodiments. The following description contains specific examples for illustrative purposes. The person skilled in the art would appreciate that variations and alterations to the specific examples are possible and within the scope of the present disclosure. The figures and the following description of the particular embodiments should not take away from the generality of the preceding summary.

The following description is divided into the following parts. In a first part, an exemplary method for modifying a retina fundus image for a deep learning model is discussed. In a second part, a training procedure which uses the modified retina fundus image as the input for a deep learning model is discussed. The deep learning model is tasked to train a DLS to screen for eye diseases. In a third part, the classification of individual diseases is discussed. In the final part, the training and validation methodology is discussed in an exemplary embodiment. Incorporating the exemplary method of the first part, a DLS is trained and validated using nearly 500,000 retinal images in an on-going "real-world" DR screening program. The results which highlight the advantages of using the DLS trained by retinal images made available through the exemplary method are discussed.

(1) Template Extraction from Retina Fundus Image

Figure 1:
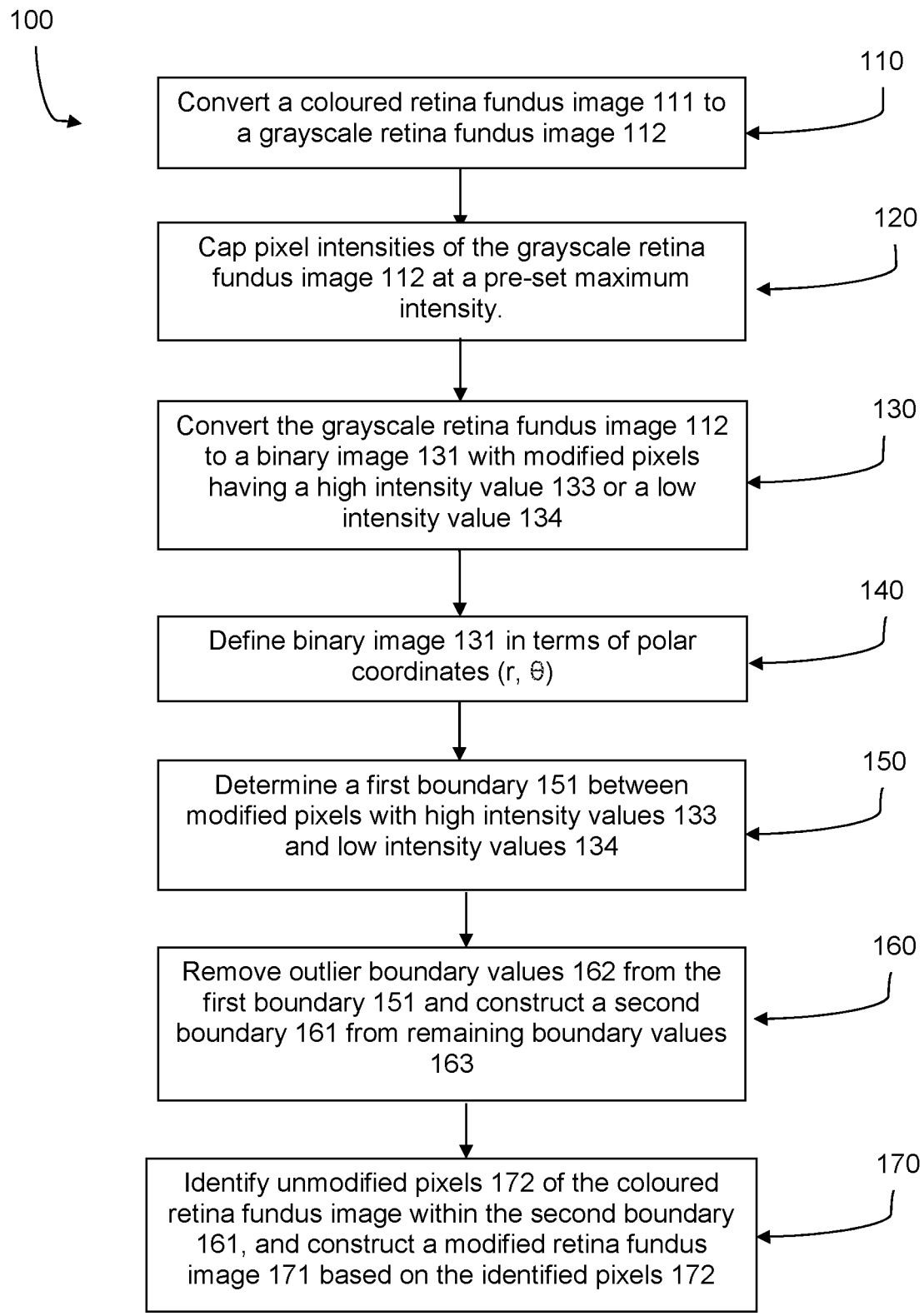
FIG. 1 is a flowchart illustrating a method of modifying a retina fundus image for a deep learning model according to a preferred embodiment.

FIG. 1 is a flowchart illustrating a method 100 for modifying a retina fundus image for a deep learning model according to a preferred embodiment. In the exemplary method 100, a coloured retina fundus image 111 having a retinal disc is first captured (for example from a patient) and presented for modification.

Figure 2:
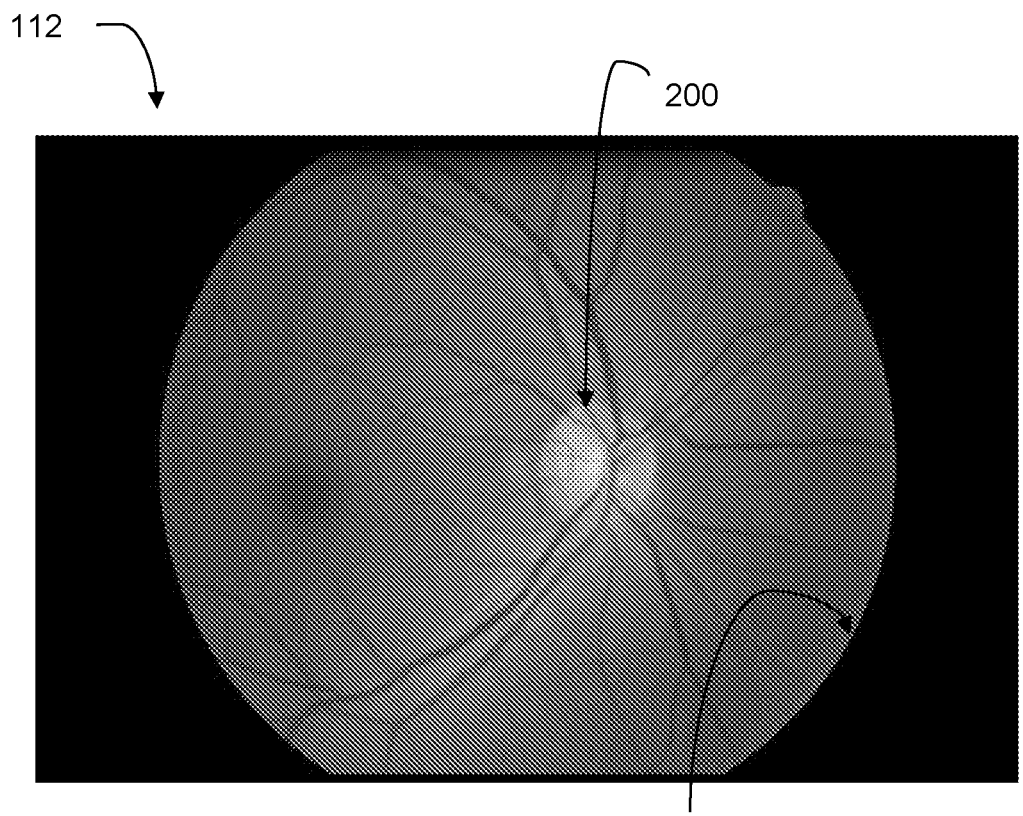
FIG. 2 is a picture of a grayscale image converted from a coloured retina fundus image from the method in FIG. 1.

At step 110, the coloured retina fundus image 111 is converted to a grayscale retina fundus image 112 by extracting and retaining only green channel values in the coloured retina fundus image 111 and representing the green channel values as levels of gray. FIG. 2 illustrates a picture of the grayscale retina fundus image 112 having an optic disc 200 and a retinal disc 210.

Other colour to grayscale conversion techniques may be utilized to convert the coloured retina fundus image 111 to a grayscale retina fundus image 112. For example, instead of using the green channel values, red channel values may be used instead.

Figure 3:
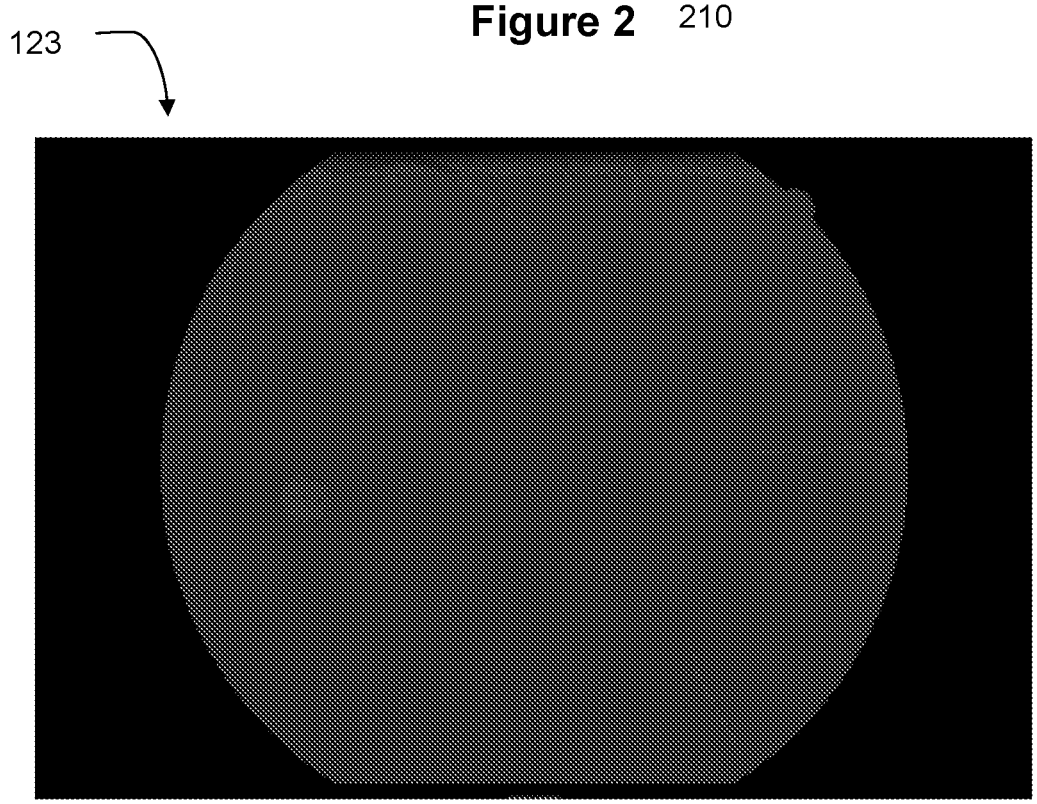
FIG. 3 shows the grayscale image of FIG. 2 with pixel intensities capped.

At step 120, pixel intensities of the grayscale retina fundus image 112 are capped at a pre-set maximum intensity of "50" and the result is illustrated in FIG. 3. The capping of the pixel intensities is performed by reducing the pixel intensities that exceed the maximum intensity to "50". Notably, the optic disc 200 (depicted in FIG. 2), usually a region containing high pixel intensities, is no longer visible in FIG. 3.

Figure 4:
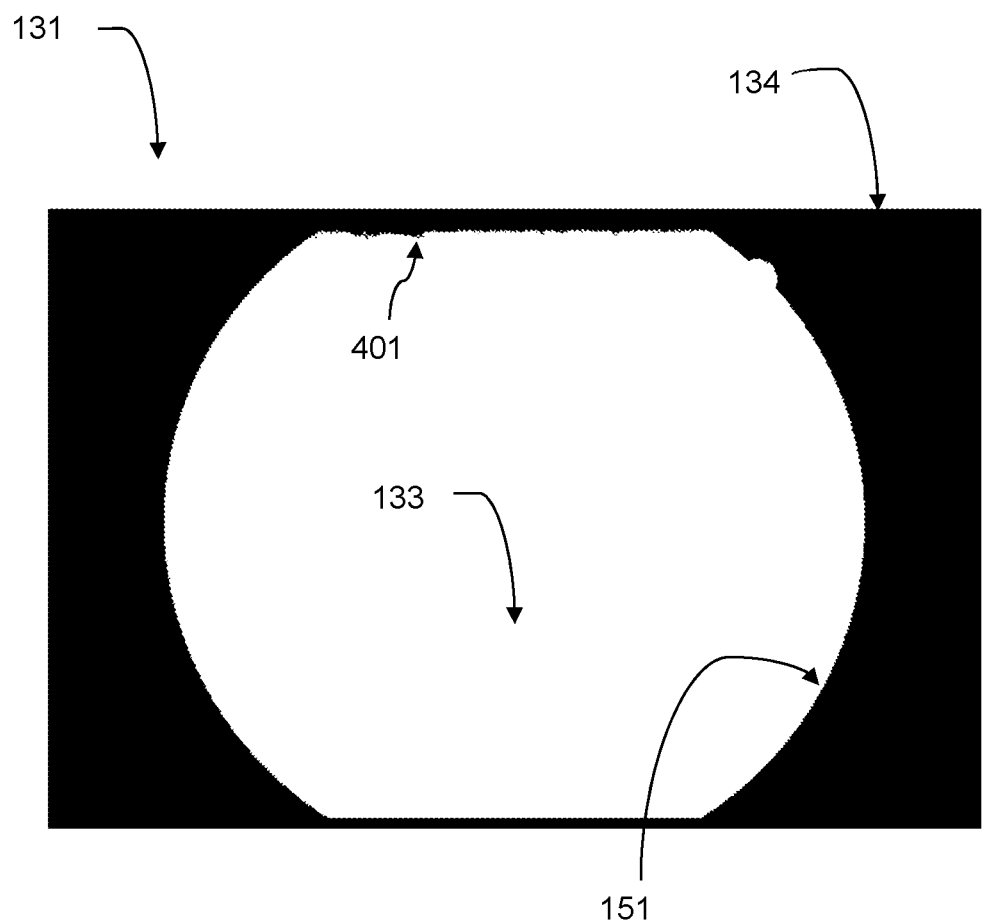
FIG. 4 is a binary image converted from the grayscale image of FIG. 3.

At step 130, using the two-class Otsu algorithm, the grayscale retina fundus image 112 is converted to a binary image 131 with modified pixels having two intensity values: a high intensity value 133 of "255", or a low intensity value 134 of "0". In other words, pixels of the retina fundus image are converted to low intensity modified pixels and high intensity modified pixels of the binary image. To elaborate, the grayscale retina fundus image 112 has gray pixels at varying levels of pixel intensities. The binary image 131 is formed by reducing the pixel intensities to two levels. This is done by assigning all pixels with pixel intensities that are above a predefined intensity threshold with a high intensity value 133 of "255" and assigning all pixels with pixel intensities that are below the predefined intensity threshold with a low intensity value 134 of "0". The intensity threshold is predefined such that it has pixel intensity between two extreme pixel intensities of the grayscale retina fundus image 112. FIG. 4 illustrates the binary image 131 with modified pixels divided into a region with high intensity value 133 and a region with low intensity value 134.

Figure 5:
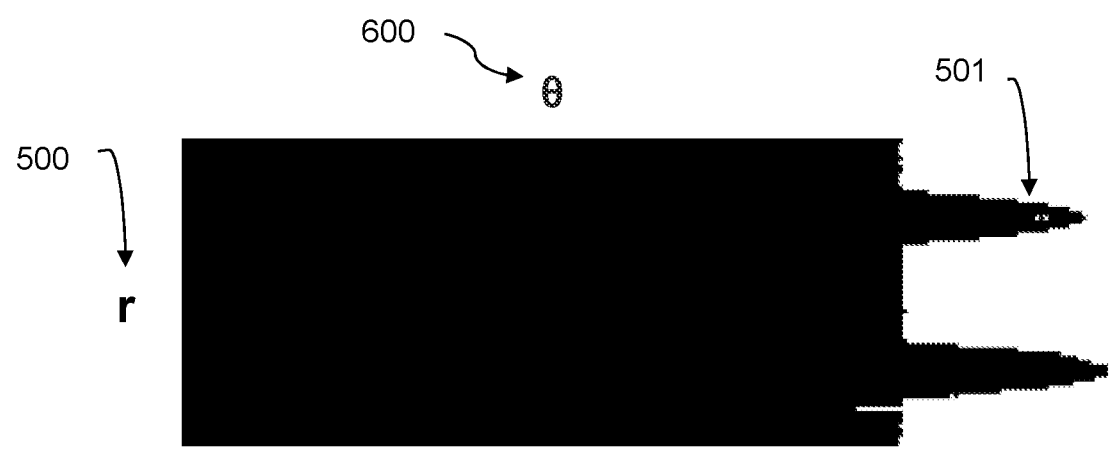
FIG. 5 depicts the binary image of FIG. 4 in polar coordinates.

At step 140, the binary image 131 is defined in terms of polar coordinates. The reference point for the polar coordinates is the centre of the binary image. In the exemplary method 100, the centre is also the midpoint of the retinal circle, as computed using all the modified pixels with high intensity value 133. FIG. 5 illustrates the binary image 131 in polar coordinates with radial coordinate, "r" 500 and angular coordinate, "θ" 600.

Figure 6:
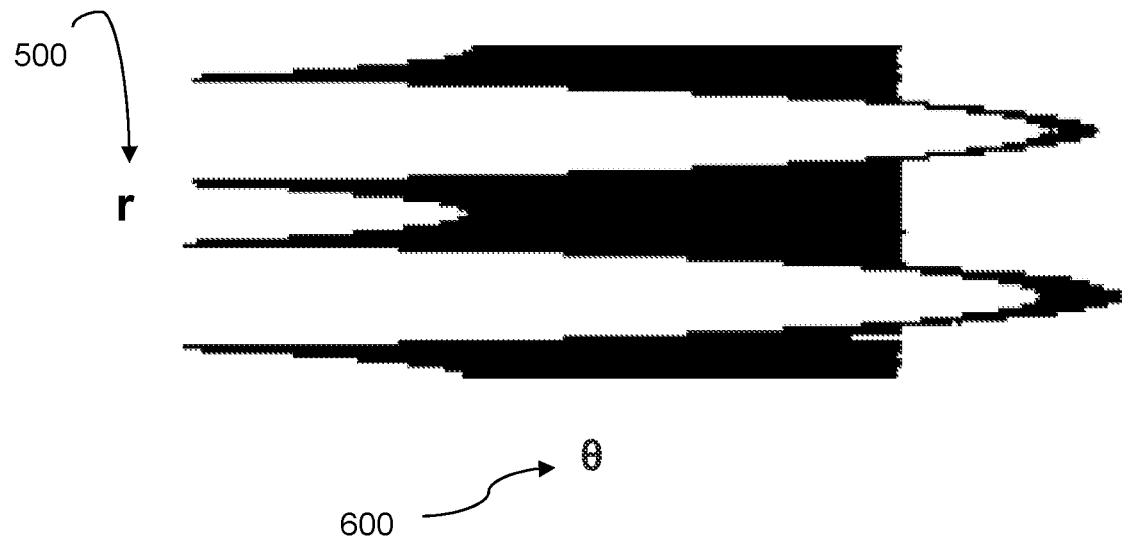
FIG. 6 depicts a first boundary of the binary image of FIG. 5 in polar coordinates.

A few white specks may be noted at peak 501 of FIG. 5 (and also FIG. 6). These white specks are a result of imperfections in the binary image 131 e.g. from the 'noisy border' 401 illustrated in FIG. 4. The imperfections appear because the coloured retina fundus image 111 used is taken from a real-world screening program which may not have needed the image taken to be perfect.

At step 150, a first boundary 151 is determined between the low intensity and high intensity modified pixels i.e. modified pixels with high intensity values 133 and low intensity values 134. Since the binary image 131 is divided into two regions, it is possible to determine the first boundary 151 such that the modified pixels with high intensity values 133 are located within the first boundary 151 while the modified pixels with low intensity values 134 are located outside the first boundary. FIG. 6 illustrates the first boundary 151 defined by boundary values in polar coordinates with radial coordinate, "r" 500 and angular coordinate, "θ" 600. The first boundary 151 defined in Cartesian coordinates is also shown in FIG. 4.

It should be noted that the first boundary defined by the boundary values may not need to be in polar coordinates. As an alternative, the boundary values may be defined in Cartesian coordinates and FIG. 4 illustrates the first boundary 151 in Cartesian coordinates. In this case, step 140 may be omitted since it is not necessary to define the binary image in polar coordinates.

Figure 7:
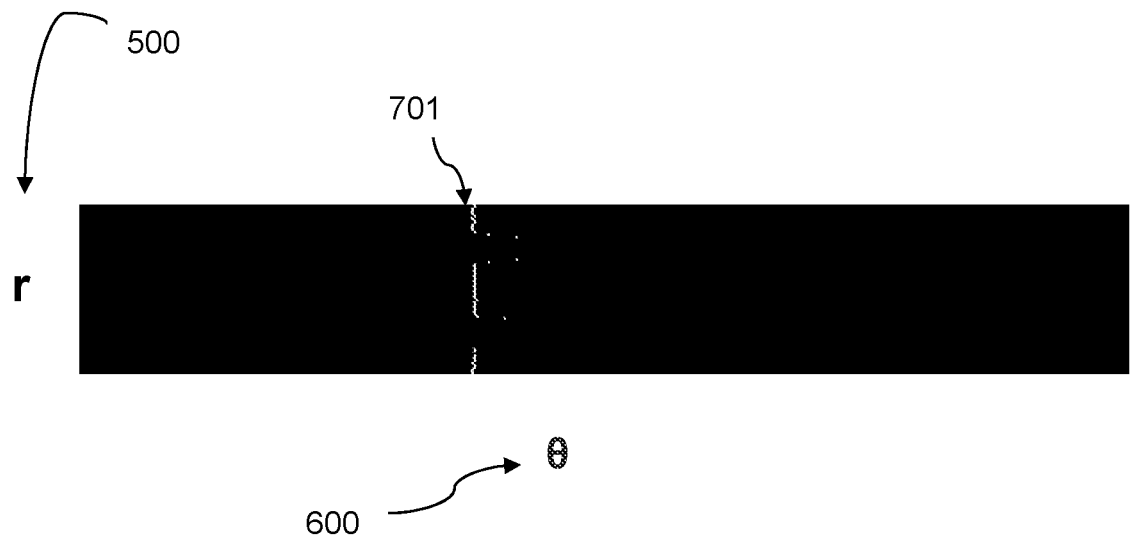
FIG. 7 depicts remaining boundary values in polar coordinates after outlier boundary values are removed from the first boundary of FIG. 6.

At step 160, outlier boundary values 162 are removed from the first boundary 151. In this embodiment, to remove the outlier boundary values, a mean radial value is computed from the boundary values and the boundary values that have radial values that are either undefined or deviate from the mean radial value by more than 10 units are deemed outlier boundary values 162. These outlier boundary values 162 are removed from the first boundary 151. FIG. 7 illustrates an intermediate-product of step 160, i.e. the remaining boundary values 163 shown in polar coordinates after the outlier boundary values 162 have been removed from the first boundary 151.

If the boundary values are defined in Cartesian coordinates, the required calculations for removing the outlier boundary values 162 may then be correspondingly performed in Cartesian coordinates by way of polar-to-Cartesian mapping.

Figure 8:
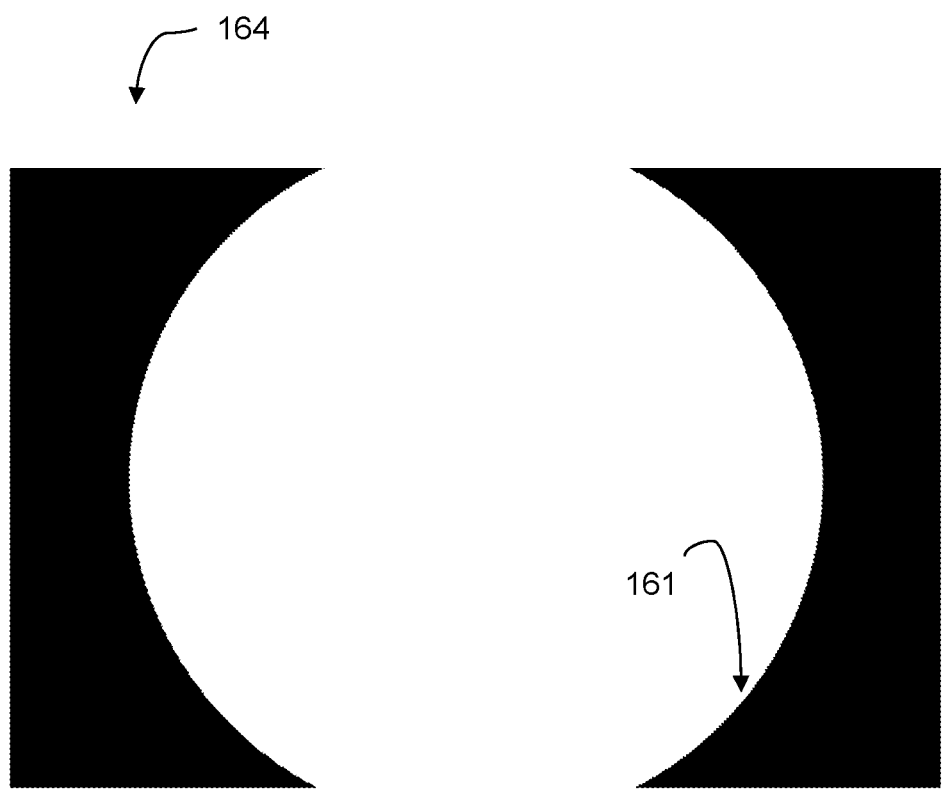
FIG. 8 is a template having a second boundary constructed from the remaining boundary values of FIG. 7.

After the outlier boundary values 162 have been removed, quadratic regression is applied to the remaining boundary values 163 to construct a second boundary 161. In the exemplary method 100, the second boundary is a fitted circle. The radius of the fitted circle is estimated from boundary values extracted from the remaining boundary values 163. The extracted boundary values can be seen as white pixels in FIG. 7. Almost all of the white pixels belong to three line segments 701, which indicate the radius of the fitted circle. The remaining white pixels to the right of the line segments 701 are outliers that are disregarded. FIG. 8 illustrates a template 164 comprising the second boundary 161 defined in Cartesian coordinates. The second boundary 161 corresponds to the estimated parameters of the retinal disc 210 (depicted in FIG. 2).

Figure 9:
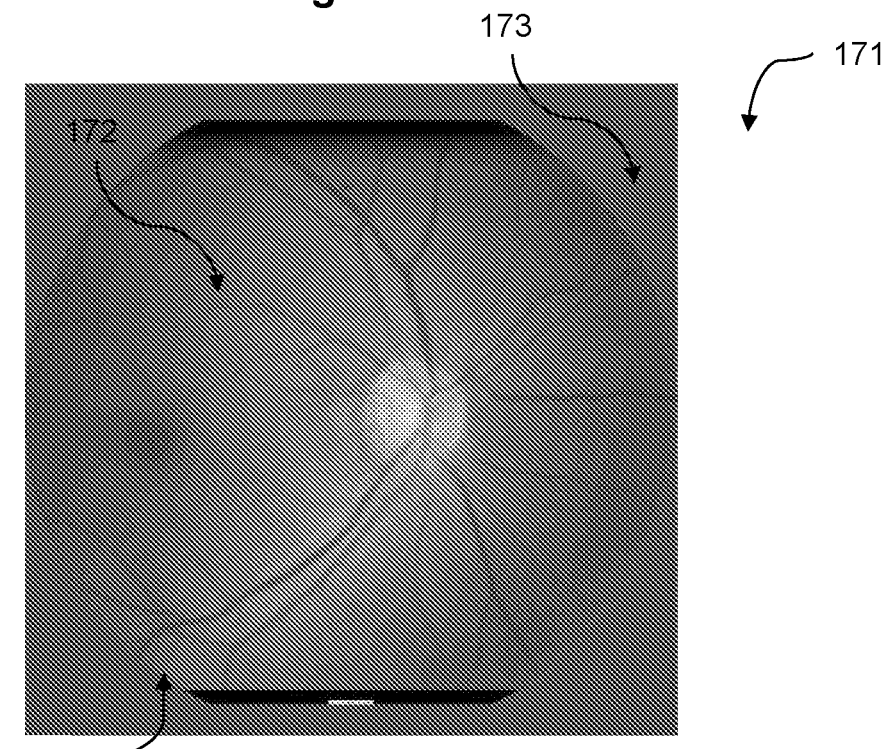
FIG. 9 is a modified retina fundus image constructed using the template of FIG. 8.

At a step 170, pixels 172 of the coloured retina fundus image 111 that would fall within the second boundary 161 of the template 164 are identified. The identified pixels 172 are copied into the second boundary 161 of the template 164. Notably, portions of the retinal disc (a gray-scale example 210 is shown in FIG. 2) are cut off at a top and bottom of the coloured retina fundus image 111. As a result, the top and bottom of the second boundary may not comprise any identified pixels, and are unoccupied. A modified retina fundus image 171 based on the template 164 is then constructed with the identified pixels 172 located within the second boundary 161. FIG. 9 illustrates the modified retina fundus image 171 constructed using the template 164 of FIG. 8.

Any unoccupied pixel within the second boundary is filled in with a background colour of the modified retina fundus image 171 and becomes a part of the background 173. While not illustrated in FIG. 9, the default background colour in the exemplary method 100 has an RGB value of [255, 0, 255].

Any background colour which allows a clear differentiation from the identified pixels 172 within the second boundary 161 may be the default colour.

Thereafter, the modified retina fundus image 171 is ready to be inputted into the deep learning model. If dimensions are not appropriate, the modified retina fundus image 171 can be rescaled to a suitable dimension e.g. "512×512" pixels.

Classification performance may further be improved by ensembling multiple training models and having each ensemble include one deep learning model that is trained on the modified retina fundus images that have undergone local contrast normalization (LCN).

Figure 10:
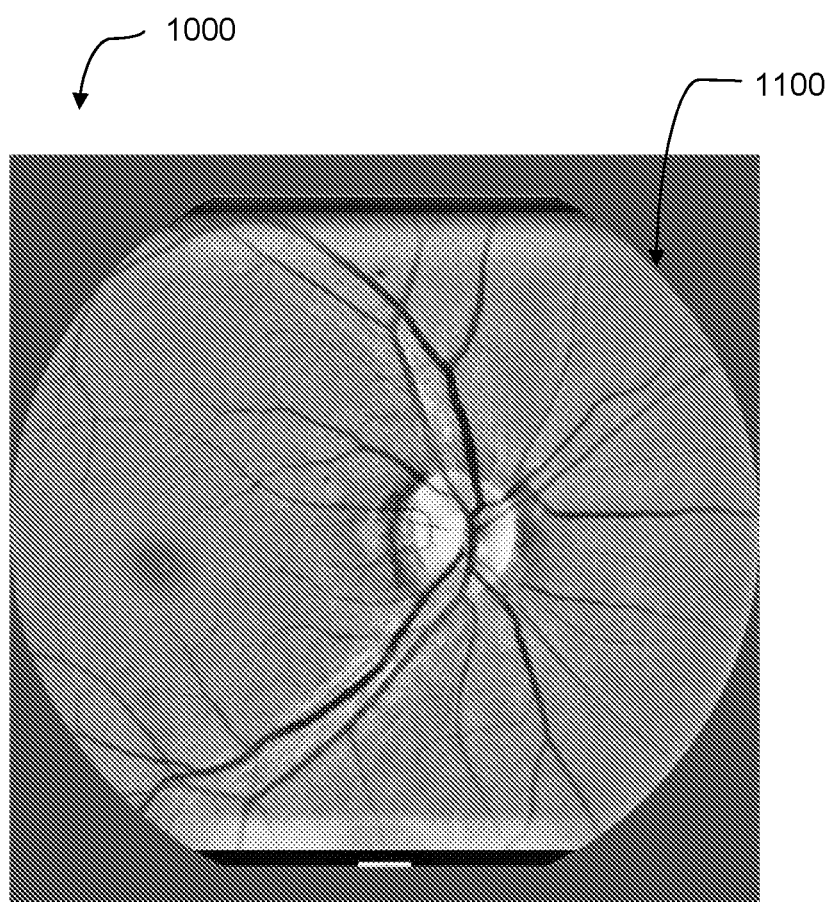
FIG. 10 is a local contrast normalized (LCN) image derived from the modified retina fundus image of FIG. 9.

FIG. 10 illustrates an LCN-modified retina fundus image 1000. To perform LCN, a large mean filter of kernel size "26×26" pixels is applied over all pixels within the retinal disc 1100 on all three RGB channels using a fast integral image implementation. The value of each pixel is set to its original value, less the mean filter value. Finally, each channel is then normalized using the mean and standard deviation statistics of all valid pixels within that channel.

Using the exemplary method 100, the training method is not constrained to using retinal fundal images captured from particular camera models or type of retina fundus cameras. A large dataset available from existing health screening programs may also be utilised to train the DLS such that the performance of the DLS in evaluating DR, GS, and/or AMD can have translational impact in real-world screening programs.

(2) Training Procedure of the DLS

The deep learning model is trained using the Caffe framework. A base learning rate of 0.001 with momentum of 0.9 is used, with a weight decay of 0.0005. A step learning rate policy with gamma parameter value of 0.98 and step size of 1000 iterations is used. The DR model is trained by sampling from the training data with all valid classes equally sampled from for 200000 iterations, and then with the original class distribution for another 300000 iterations. The AMD and GS models are trained by sampling from all valid classes equally sampled from for 200000 iterations. These training procedures produce optimal results from all attempted variations, by empirical validation.

To incorporate further variation into the training data, the input images are adjusted on-the-fly in the following ways:
Overall scaling, with uniform scale factor from 0.95 to 1.05
Overall rotation, with uniform rotation factor from 0 to 359 degrees
Horizontal flipping, with probability 0.5
Brightness adjustment, with uniform scale factor from 0.7 to 1.3

(3) Classification of Individual Diseases

Each model has 'n' output nodes, corresponding to the clinically-relevant severity classes for the targeted disease, in order of increasing severity. For example, the DR model has five output nodes indexed from '0' to '4', with '0' representing 'No DR', '1' representing 'Mild DR', '2' representing 'Moderate DR', '3' representing 'Severe DR', and 4 representing 'Proliferative DR'.

After being trained, the output of the model can be interpreted as a probabilistic prediction of the class of the input image. For example, if the five-node output for the DR model is (0.80,0.10,0.05,0.03,0.02), it projects a 80% chance that the image is 'No DR', a 10% change of 'Mild DR', a 5% chance of 'Moderate DR', a 3% chance of 'Severe DR' and a 2% chance of 'Proliferative DR'.

For evaluation purposes, these values are converted into a single scalar value, by multiplying the output value of each node with the index of the node. Continuing from the above example, the model score would be (0.80*0+0.10*1+0.05*2+0.03*3+0.02*4)=0.37. The model ensemble score value is defined as the mean of the constituent model scores.

For each eye, at least two images corresponding to two standard fields of view—OD-centered and macula-centered—are evaluated by the deep learning model. Each of these images is first classified by a gradability model and a non-retinal model, to determine whether it is acceptable for further evaluation. The eye is rejected and referred if all corresponding images are rejected. If there are sufficient images to proceed, the model ensemble score value of the eye is defined as the mean of the model ensemble score value of the individual images.

For each individual disease, a score threshold is determined through empirical validation on an unseen validation dataset. Eyes with a score at or above the threshold are then classified as positive for the disease, and are classified as negative for the disease otherwise.

(4) Training Methodology

In the following section of the description, a training and validation methodology for a DLS is discussed. The DLS is trained and validated to detect referable DR using nearly 500,000 retinal images, primarily in an on-going "real-world" national DR screening program, with further external validation of the DLS in 10 additional datasets of multiple ethnicities (with varying fundi pigmentation) in different settings (community, population-based and clinic-based, with different retinal cameras). The performance of the DLS in detecting two outcomes: referable DR, where patients are referred from the screening program to ophthalmologists, and VTDR, which require more urgent referral and management, is evaluated. A secondary analysis is performed to determine the ability of the DLS in detecting referable glaucoma suspects (GS) and referable AMD as part of the DR screening program. Lastly, the performance of the DLS in detecting overall referable status (referable DR, GS, AMD) is evaluated, and the DLS is applied to two DR screening models: a "fully automated" screening model useful in communities with no existing screening programs, and a "semi-automated" model in which referable cases from the DLS have a secondary assessment by professional graders.

Training Datasets of the DLS

In this embodiment, a total of 493,667 retinal images for developing the DLS, including: 76,370 and 112,648 for DR; 125,189 and 71,896 for referable GS and; 71,616 and 35,948 for referable AMD are used for training and validation, respectively. FIGS. 11A and 11B provide an overview on the number of images in each of the training and validation datasets for referable DR, GS and AMD (Table 1).

The DLS for referable DR is developed and trained using retinal images of patients with diabetes who participated in an on-going national DR screening program between 2010 and 2013 (SiDRP 2010-13) which used digital retinal photography, a tele-ophthalmology platform and assessment of DR by trained professional graders. For each patient, two retinal photographs (optic disc and fovea) are taken of each eye. Referable eyes are re-graded by senior professional graders; if there is discordant findings, arbitration is performed by retinal specialists. FIGS. 12A and 12B summarizes the training and validation datasets for DR (Table 2). Notably, in the primary validation dataset, i.e. SiDRP 2014-2015, 6291 patients were repeats from SiDRP 2010-2013 while 8,589 were unique patients. Unique patients are the patients who did not appear in the SiDRP 2010-2013 screening program and therefore, there are no overlaps in the validation dataset of SiDRP 2010-2013 and the training dataset of SiDRP 2014-2015 for these patients.

For referable GS and AMD, the DLS is trained using images from SiDRP 2010-13 and several additional population- and clinic-based studies of Singapore Chinese, Malay, Indian patients with GS and AMD. FIG. 13 summarizes the training dataset for GS and AMD (Table 3).

Architecture of Deep Learning Model

Figure 14:
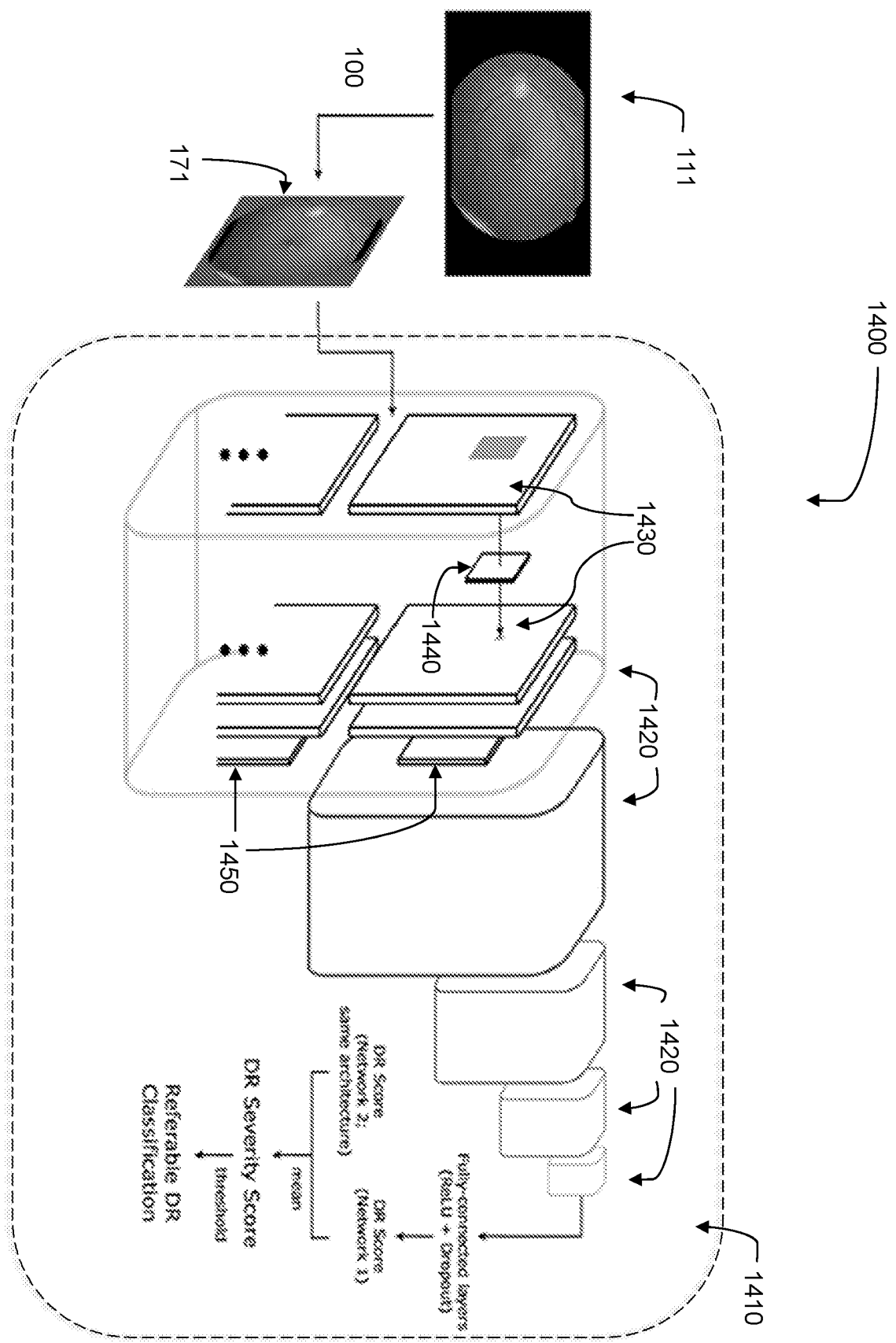
FIG. 14 depicts the architecture of an exemplary CNN of the deep learning model that will be trained using either the modified retina fundus image or LCN image of FIGS. 9 and 10 respectively.

Using the exemplary method 100 of FIG. 1, the coloured retina fundus image 111 is modified to the modified retina fundus image 171 with dimensions scaled to 512×512 pixels before it is utilized by a deep learning model. The deep learning model is composed of eight convolutional neural networks (CNN), all using an adaptation of the VGGNet architecture: (a) an ensemble of two networks for the classification of DR severity, (b) an ensemble of two networks for the identification of referable GS (c) an ensemble of two networks for the identification of referable AMD, (d) one network to assess image quality; and (e) one network to reject invalid non-retinal images. An exemplary CNN 1410 of the deep learning model used to trained the DLS 1400 is illustrated in FIG. 14.

VGGNet produces state-of-the-art performance on the classification of retina images. The training of a CNN 1410 to model DR is achieved by presenting the network with batches of labeled training images. The CNN 1410 then incrementally learns the key characteristics of images belonging to each class. Multiple CNNs 1410 are trained to obtain an image score by assembling the individual CNN scores. Likewise, the eye-level classification is produced using all available images of an eye that are of acceptable quality, and apply score thresholds determined from the training data.

As a preparatory step, each retinal photograph is first automatically segmented to extract only the retina disc. This circular region of interest is then uniformly rescaled to fit a standardized square template of dimension 512×512 pixels. The RGB values of the modified retina fundus image 171 are then input as the three channels of the first layer of the relevant convolutional networks 1410. The input layer is followed by a succession of modules 1420. Each module 1420 begins with multiple convolutional layers 1430 that learn features at the current scale. Each convolutional layer 1430 contains a collection of feature maps, which values are communicated to the feature maps in the next layer 1430 through 3×3 weight kernels 1440. Each module 1420 ends with a 2×2 max-pooling layer 1450 that effectively downsamples the feature dimensions by a factor of two, such that they can serve as the inputs to the next module 1420. The series of modules 1420 terminates when the features output by the last module 1420 are features of dimension 1×1. Standard ReLU rectification and dropout layers are then applied, before a final softmax output layer, that contains one output node for each class trained for. Each convolutional network 1410 contains five such modules 1420, for a total of 19 layers.

The training procedure for each convolutional network 1410 involves repeatedly randomly sampling a batch of images from the training set, together with their ground truth classification. The weight values of the convolutional network 1410 are then adjusted by gradient descent, which incrementally improves the general association between images of a certain class, and the value of their corresponding output node. Concurrently, the convolutional network 1410 automatically learns useful features at each scale represented by its models, from the smallest-possible pixel level, to scales approaching that of the original input. To expose the convolutional network 1410 to additional plausible input feature variations, a limited family of transformations is applied to the input images, involving mirroring, rotation, and scaling by a small degree. Each network 1410 is trained approximately to the convergence of its performance, on a small held-out validation set.

For the classification of DR severity, an ensemble of two convolutional networks 1410 is used. The modified retina fundus images 171 are provided as input to one network 1410, while locally contrast-normalized images (LCN) 1000 is provided as input to the other network 1410. The output nodes of each network 1410 were indexed according to increasing severity of DR class, from 0 to 4. This allows the predicted DR severity to be represented by a single scalar value, by summing the product of the value of each output node, with its index. The final DR severity score is then the mean of the outputs of the two convolutional networks 1410. Classification of test images is then achieved by thresholding the DR severity score for desired sensitivity/specificity performance, as estimated from the validation set. A threshold of 0.9 is selected as being adequate for screening purposes. For the classification of AMD and glaucoma severity, a similar procedure is followed, except that each of these conditions admits only three severity classes, from 0 to 2. A threshold of 0.40 is selected for AMD, and 0.70 for glaucoma.

Additionally, convolutional networks 1410 are trained to reject images for insufficient image quality, as well as for being invalid input (i.e. not being a retinal image). For the latter model, a broad variety of natural images is used as the negative class, in training. Images rejected by either of these models are considered as being recommended for further referral, for the purposes of computing the experimental results. Once an image is analyzed, a report will be generated for the users. On average, the deep learning model takes approximately 5 minutes to analyze 1000 images (0.3 seconds per image), using a single graphic processing unit (GPU).

Validation Datasets for Referable DR, VTDR, Referable GD and Referable AMD

Details of the validation dataset are summarized in FIGS. 11A and 11B. For DR the primary validation dataset is the same DR screening program among patients seen between 2014 and 2015 (SiDRP 2014-15). The primary analysis determines if the DLS 1400 is equivalent or better than the professional graders in detecting referable DR and VTDR in the primary validation dataset.

The DLS 1400 is also externally validated using 10 additional multi-ethnic cohorts with diabetes participants from different settings (community, population-based and clinic-based). Dataset 1 consists of Chinese participants with diabetes screened in the community by the Zhongshan Ophthalmic Center, Guangdong, China. Datasets 2-4 were Chinese, Malay, and Indian participants with diabetes recruited from the population-based Singapore Epidemiology of Eye Disease (SEED) program. Datasets 5 and 6 was population-based studies of Chinese and African-American participants from the Beijing Eye Study (BES) and the African American Eye Study (AFEDS) respectively. Datasets 7 to 10 were clinic-based diabetes studies among Caucasians patients from the Royal Victorian Eye and Ear Hospital, Melbourne, Australia, Hispanic patients from Instituto Mexicano de Oftalmologia Eye Center, Mexico, and Chinese patients from the Chinese University of Hong Kong, and University of Hong Kong. There are no overlaps of patients in all datasets.

For secondary analysis of referable GS and AMD, the DLS 1400 is also validated in the primary validation cohort of SiDRP 2014-15.

Finally, using the same primary validation cohort, comparison of the two DR screening models (fully automated vs semi-automated model for detection of overall referable status (referable DR, GS or AMD) is performed.

Retinal Photography Protocols

Different cameras are used across the cohorts. Non-mydriatic 2-field (optic disc and fovea-centerd) retinal photography is performed for all eyes of SiDRP, Guangdong Chinese, and Mexican Hispanic participants. Mydriatic 2-field retinal photography is performed for Singaporean Chinese Malay, Indian, Beijing Chinese, African Americans, Caucasians and Hong Kong Chinese patients. Retinal images are not captured in a standardized fashion across the sites (i.e. different flash setting, status of pupil dilation, width of field (35 degrees and 45 degrees) and cameras (Topcon, FundusVue, Canon and Carl Zeiss). All retinal images are with JPEG compression format, with resolutions between 5-7 megapixels, except for Hispanic images (mostly <1 megapixel).

Definition of Referable DR, VTDR, Referable GS and Referable AMD

DR levels from all retinal images are defined using the International Classification DR Scale. Referable DR is defined as a diabetic retinopathy severity level of moderate non-proliferative DR (NPDR) or worse, diabetic macular edema (DME) and/or ungradable image and; VTDR, as severe NPDR and PDR. DME is assessed as present if hard exudates are detected at the posterior pole of the retinal images. If more than one-third of the photo is obscured, it will be considered as "ungradable" and the individual considered to have referable DR. Referable GS is defined as vertical cup/disc diameter ratio of ≥0.8, focal thinning or notching of the neuroretinal rim, optic disc haemorrhages, or localized retinal nerve fibre layer defects. Using the Age-Related Eye Disease Study (AREDS) grading system, referable AMD is defined as the presence of intermediate AMD (numerous medium-sized drusen, 1 large drusen >125 um in greatest linear diameter, non-central geographical atrophy (GA) and/or advanced AMD (central GA or neovascular AMD).

Reference Standards

For the primary validation dataset (SiDRP 2014-15), the reference standard is a retinal specialist grading. The performance of the DLS 1400 is evaluated to this reference standard. The performance of DLS 1400 is then compared to that of the professional graders' assessment, with reference to the retinal specialist grading.

For all other retinal images from validation datasets 1 to 10 (presented in FIG. 11A), trained professional graders in their own countries are the reference standard and the performance of the DLS 1400 is evaluated to this standard.

For secondary analysis on referable GS and AMD, the reference standard is a glaucoma specialist and a retinal specialist, respectively. For overall referable status using fully automated versus semi-automated model, the reference standard is a retinal specialist (for referable DR and AMD) and glaucoma specialist (referable GS).

Statistical Analysis

Initially, the area under the curve (AUC) of the receiver operating characteristic (ROC) curve of the DLS 1400 on the training dataset of the SiDRP 2010-13 is calculated across a range of classification thresholds. The classification threshold that achieved a pre-determined optimal sensitivity of 90% for detecting referable DR and VTDR is then selected. It is hypothesized that the performance of the DLS 1400 is comparable to the professional graders' performance, and the threshold point of the DLS 1400 is pre-set at a sensitivity of 90% (SiDRP graders had previously achieved this level). Similarly, for referable GS and AMD, the threshold point is pre-set at sensitivity and specificity of 90% and 80%, respectively. The pre-set threshold for sensitivity or specificity of DLS 1400 can be adjusted depending on specific needs of screening programs.

For the primary analysis, the DLS 1400 performance in the setting of the ongoing DR screening program (SiDRP 2014-15, primary validation set) is evaluated by determining whether the DLS 1400 achieved optimal performance and is equivalent or superior to the assessment of DR by professional graders in the screening program. Thus, the AUC, sensitivity, specificity, positive predictive value (PPV) and negative predictive value (NPV) of DLS 1400 in detecting referable DR and VTDR is computed to the reference standard (retinal specialist) at individual eye levels, and the DLS 1400 is then compared with the assessment by professional graders. For comparing diagnostic tests, computation of 95% confidence intervals (CI), absolute difference in the true positive fraction (TPF, sensitivity) and false positive fraction (FPF, 1-specificity) between the DLS 1400 and professional graders, with reference to the gold standard (retinal specialist) is recommended. McNemar's test is performed for paired proportions to check for significant differences in each fraction between DLS 1400 and graders.

The following subsidiary analyses are performed. First, patients who appeared both in the SiDRP 2010-13 training set and primary validation set of SiDRP 2014-15 (n=6291, who were seen more than once in SiDRP) are excluded, and the above analyses are repeated to avoid data contamination between training and validation dataset. The patient is treated as having "referable DR" if either eye had referable DR. Second, the DLS 1400 performance is evaluated only in higher quality images with no media opacity (e.g. cataracts), as noted by professional graders. Third, the AUC sub-groups stratified by age, gender and glycemic control are computed to evaluate DLS 1400 performance on patients' with different characteristics. Fourth, all analyses are repeated on the 10 multi-ethnic validation sets (Datasets 1-10, described above), with reference to trained graders.

For the secondary analysis, the DL 1400S performance in detecting referable GS and AMD, is evaluated with reference to a glaucoma specialist and a retinal specialist, respectively using the primary validation dataset (SiDRP 2014-15).

Figure 15:
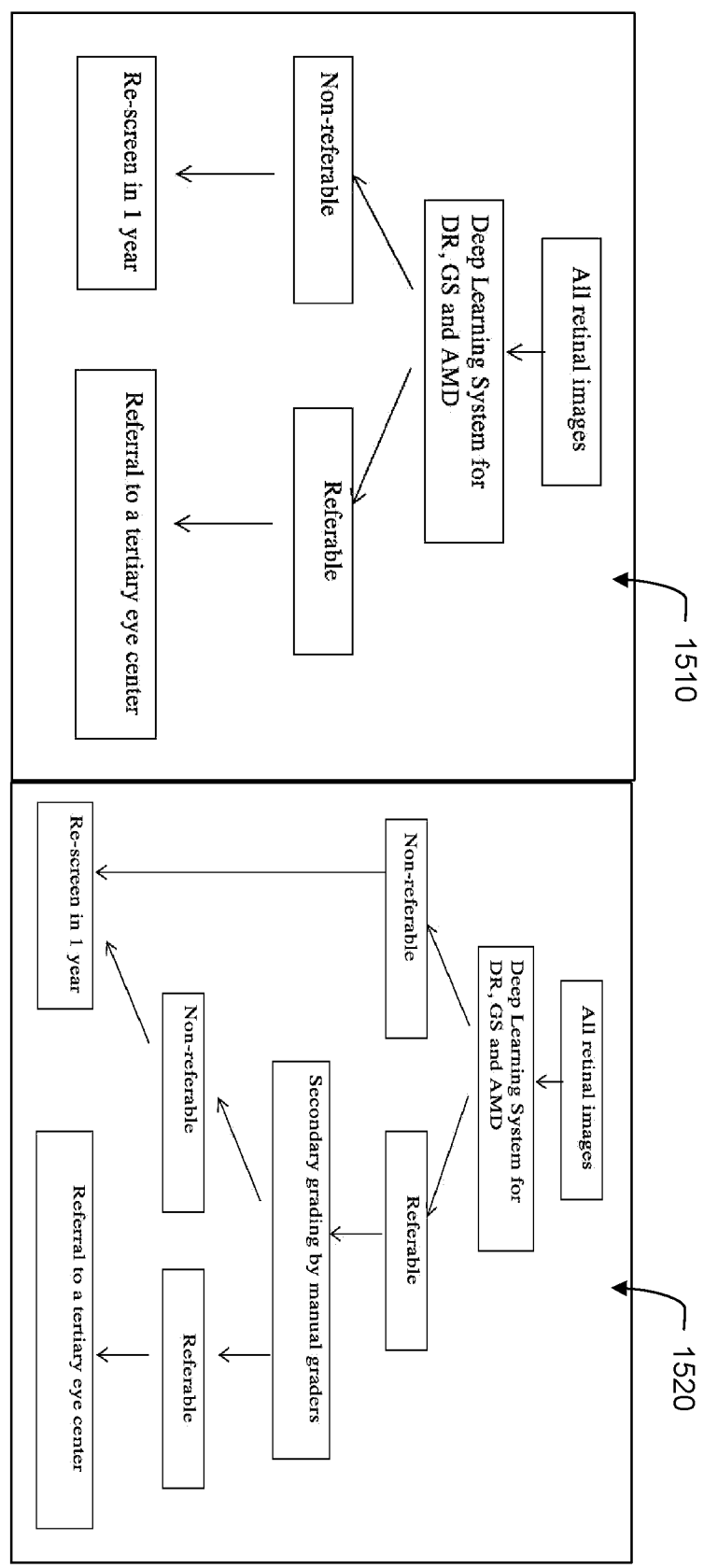
FIG. 15 depicts flowcharts of two different screening models which use the DLS trained using the architecture of FIG. 14.

Lastly, a comparison of the two different screening models: "fully automated" versus "semi-automated" in detection of overall referable status (referable DR, GS or AMD) is done. FIG. 15 illustrates 2 flowcharts for the two different screening models.

Flowchart A shows the fully automated system 1510. In the fully automated system 1510, all retinal images are analyzed by the DLS 1400 for DR, GS and AMD. The retinal images are classified as 'referable' if any one of the 3 conditions: referable DR, referable GS or AMD is detected. The patient is then referred to a tertiary eye center. If the retinal images are classified as 'non-referable', then the patient is scheduled to be rescreened in a year. In the fully automated system 1510, no human graders are needed. Flowchart B shows the semi-automated system 1520. The semi-automated system 1520 follows the same procedure as the fully-automated system 1510 except where retinal images are classified as 'referable', the retinal images go through a secondary grading by manual graders where the retinal images are reclassified as either 'referable' or 'non-referable'.

Asymptotic two-sided 95% CI which adjusted for clustering by patients are calculated and presented for proportions (sensitivity, specificity, PPV and NPV) and AUC respectively. In a few exceptional cases that the estimate of sensitivity is at the boundary of 100%, the exact Clopper-Pearson method is used instead to obtain CI estimates. All analyses are performed using Stata version 14 (StataCorp, College Station, Tex., USA).

Results

Amongst 76,370 images (38,185 eyes) in the training dataset, 11.7%, 3.0%, 1.4% had any DR, referable DR and VTDR, respectively, while in the combined primary and external validation dataset of 112,648 images (59,324 eyes), these are 14.8.3%, 5.3% and 1.5%, respectively. The DR results are summarized in FIGS. 12A and 12B. For GS and AMD, 2,658 images (1,329 eyes) and 2,499 images (2,499 eyes) are considered 'referable' for each condition, respectively. The GS and AMD results are summarized in FIG. 13. FIG. 16 illustrates the overall demographics, diabetes history and systemic risk factors of patients attending SiDRP 2014-15 (primary validation set) (Table 4).

FIG. 17 illustrates the diagnostic performance of DLS 1400 compared to professional graders, with reference to the retinal specialist standard, using the primary validation dataset (SiDRP 2014-15) (Table 5). As illustrated in FIG. 20A-20O (Graph A), the AUC of the DLS 1400 is 0.936 for referable DR and 0.958 for VTDR. Sensitivity and specificity of DLS 1400 in detecting referable DR is comparable to professional graders (DLS: 90.5%/91.6% versus graders: 91.2%/99.3%). For VTDR, the sensitivity and specificity of DLS 1400 is 100% and 91.1% respectively, compared to 88.5% and 99.6% in graders. Amongst eyes with referable DR, the DME detection rates are 92.1% and 98.2% for DLS 1400 and graders, respectively. The DLS 1400 is more sensitive (100% vs 88.5%) in detecting VTDR, with a TPF that is greater by 11.5% (Table 5).

Figure 20B:
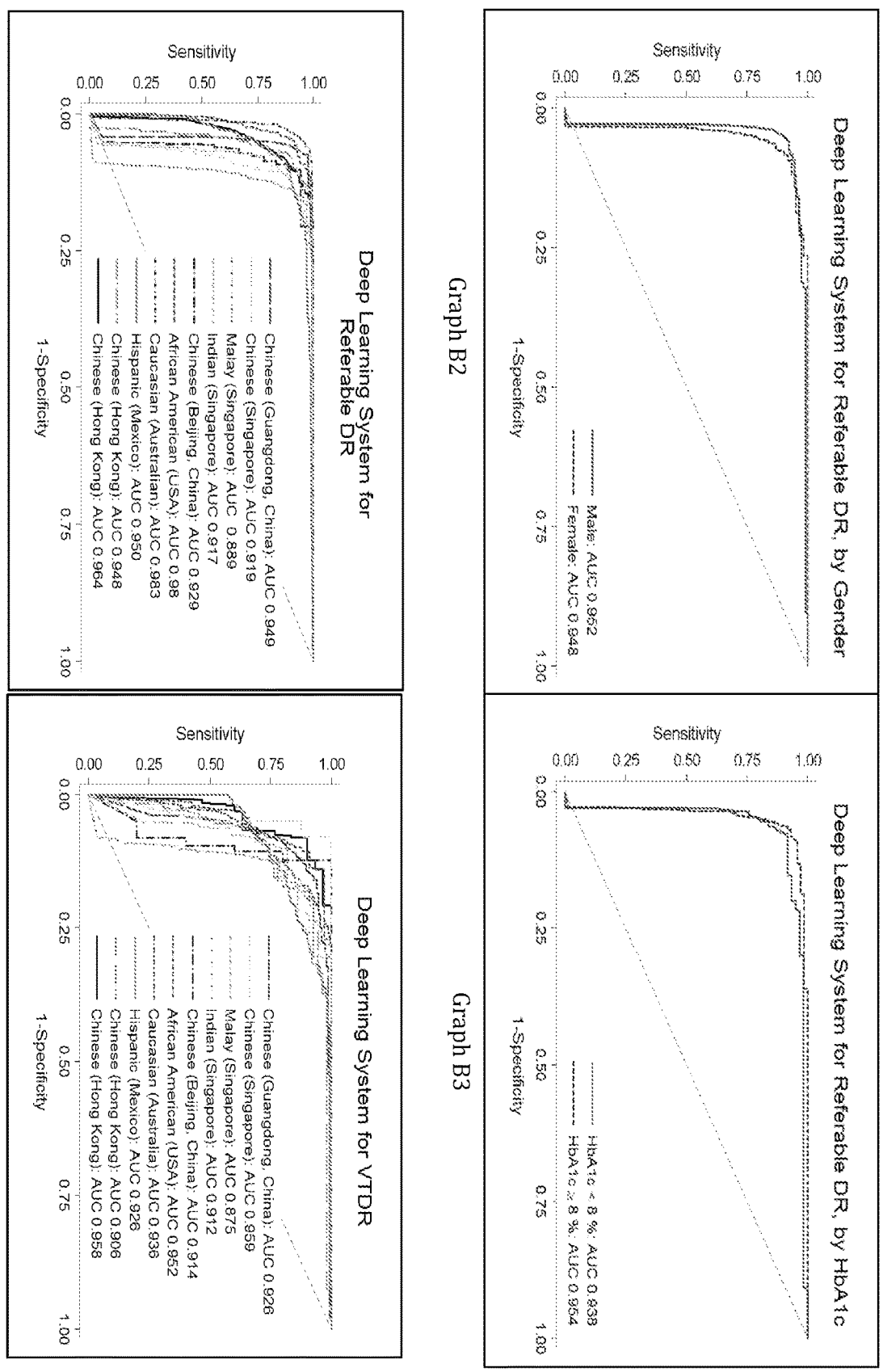

In subsidiary analyses, the robustness of the DLS 1400 is confirmed in several ways. First, the DLS 1400 showed comparable performance to professional graders in all 8,589 unique patients of SiDRP 2014-15 (with no overlap with training set), with results similar to the primary analysis as illustrated in FIG. 18 (Table 6). Second, in the subset analysis of 97.4% eyes (n=35,055) with excellent retinal image quality (no media opacity), the AUC of the DLS 1400 for referable DR and VTDR increased to 0.949 (95% CI: 0.940-0.957) and 0.970 (0.968-0.973), respectively. Third, DLS 1400 showed comparable performance in different sub-groups of patients stratified by age, gender and glycemic control as illustrated in FIGS. 20A-20C (Graphs B1, B2, B3 respectively). Fourth, the DLS 1400 was robust with respect to multi-ethnic populations of different communities, clinics and settings. Among the additional validation datasets presented in FIG. 11A (Datasets 1 to 10), the AUC, sensitivity and specificity of detecting referable DR ranged from 0.889 to 0.983; 91.8% to 100% and; 73.3% to 92.2% respectively; with VTDR detection rate of 93% to 100% as illustrated in FIGS. 19A and 19B (Table 7). FIGS. 20A-20C (Graph C1 and C2) presents the ROC curves for DLS 1400 for detecting referable DR and VTDR in the 10 validation cohorts.

For secondary analysis, the AUC, the sensitivity and specificity of DLS 1400 were 0.942, 96.4%, 87.2% for referable GS and 0.931, 93.2% and 88.7% for referable AMD, respectively as illustrated in FIG. 21 (Table 8).

It is shown that the DLS 1400 can be used in two screening models: the fully automated model had sensitivity and specificity of 93.0% (95% CI 91.5%-94.3%) and 77.5% (95% CI 77.0%-77.9%), respectively to detect overall referable cases (referable DR, GS or AMD) while the semi-automated model had 91.3% (95% CI 89.7%-92.8%) and 99.5% (95% CI 99.5%-99.6%), respectively.

In all validation sets (datasets 1-10) shown in FIG. 11A, the repeatability of DLS 1400 was 100% when the same images were tested twice, with DLS 1400 producing grading outcomes that were identical between the first and repeated readings for all images for referable DR, VTDR, GS and AMD.

Using nearly half a million retinal images from multi-ethnic datasets across the world, the use and applicability of the DLS 1400 for DR screening is shown in several key features. First, the DLS 1400 is validated in an on-going national screening DR program in Singapore, in which patients are not pre-selected based on criteria. The performance of the DLS 1400 is shown to be comparable to the current DR screening system based on assessment of retinal images by trained professional graders. The consistency and diagnostic performance of the DLS 1400 is validated using 10 additional external validation datasets with different ethnicities and settings (patients' demographics, glycemic control, status of pupil dilation, retinal cameras, flash settings and width of field for retinal images). Second, the diagnostic performance of the DLS 1400 is excellent not only when screening for referable DR and VTDR, but also two common vision-threatening conditions (referable GS and AMD) (all AUCs>0.92; all sensitivity >90%, all specificity >85%) which is important for clinical acceptability of such DLS 1400 for adoption in the real world. Finally, the DLS 1400 can be deployed in two DR screening models: a "fully automated" screening model which showed optimal diagnostic performance to detect all 3 conditions in communities without any existing DR screening programs or a "semi-automated" model in which DR screening programs already exist (e.g., UK, Singapore) but the DLS 1400 can improve efficiency, reduce cost and conserve human resources. Adoption of DLS 1400 system into real-world settings can therefore increase the number of screening episodes without the current need for infrastructure and human resources.

Using the exemplary method 100 to modify retinal images to a form that is suitable for input into the DLS 1400, the DLS 1400 can be applied to screen a wide variety of retinal photograph types, due to the diversity and size of the training datasets used during model construction. Consequently, the DLS 1400 has consistent diagnostic performance across different patient profiles, with varying image quality, different camera types, systemic glycemic control level and across multiple ethnicities (i.e. from darker fundus pigmentation in Africans Americans and Indians to lighter fundus in Caucasians). In addition, the DLS 1400 diagnoses multiple common eye diseases (referable DR and VTDR, referable GS and AMD) to acceptable clinical performance guidelines.

It is noted that minority groups in US (e.g. Hispanics and African Americans) have lower DR screening rates. The DLS 1400 showed excellent performance for the detection of referable DR in African Americans and Hispanics, with corresponding AUCs of 0.980 and 0.950, respectively as shown by data presented in FIGS. 19A and 19B (Table 7). The VTDR detection rate was >97% in both ethnic groups. The use of this DLS 1400 may therefore bridge the screening gap by improving accessibility.

The DLS 1400 may be utilized as an automated first-cut tool for general eye screening of large populations. The DLS 1400 may also be utilized as an automated assistant for clinicians and graders to get a second opinion. Alternatively, the DLS 1400 may also be utilized as a standalone on-demand eye diagnosis service over the Internet.

The invention claimed is:

1. A method of modifying a retina fundus image for a deep learning model, the method comprising:
   (i) converting a retina fundus image to a binary image, pixels of the retina fundus image being converted to low intensity modified pixels and high intensity modified pixels of the binary image;
   (ii) determining a first boundary between the low intensity modified pixels and the high intensity modified pixels;
   (iii) removing outlier boundary values from the first boundary and constructing a second boundary from remaining boundary values, the second boundary corresponding to estimated parameters of a retinal disc;
   (iv) identifying the pixels of the retina fundus image that are within the second boundary; and
   (v) constructing a modified retina fundus image for the deep learning model, the modified retina fundus image comprising the identified pixels.

2. A method according to claim 1, wherein the retina fundus image is a grayscale image.

3. A method according to claim 2, further comprising converting a coloured retina fundus image to the grayscale retina fundus image using green channel values prior to converting the retina fundus image in (i).

4. A method according to claim 1, wherein converting the retina fundus image in (i) comprises classifying the pixels of the retina fundus image with corresponding intensity values below a predefined intensity threshold as the low intensity modified pixels and the pixels of the retina fundus image with corresponding intensity values above the predefined intensity threshold as the high intensity modified pixels.

5. A method according to claim 4, wherein each of the low intensity modified pixels has an intensity value of 0 and each of the high intensity modified pixels has an intensity value of 255.

6. A method according to claim 1, wherein converting the retina fundus image in (i) is performed using two-class Otsu algorithm.

7. A method according to claim 1, further comprising capping pixel intensity of the retina fundus image at a pre-set maximum intensity, prior to converting the retina fundus image in (i).

8. A method according to claim 7, wherein the maximum intensity is pre-set to 50.

9. A method according to claim 1, further comprising defining the binary image in terms of polar coordinates, prior to determining the first boundary in (ii).

10. A method according to claim 1, wherein the high intensity modified pixels are located within the first boundary and the low intensity modified pixels are located outside the first boundary.

11. A method according to claim 1, wherein determining the first boundary comprises defining the first boundary in terms of boundary values in polar coordinates.

12. A method according to claim 11, wherein removing outlier boundary values comprises:
   computing a mean radial value from the boundary values; and
   removing the boundary values with radial values that are undefined or deviate from the mean radial value.

13. A method according to claim 12, wherein the boundary values which deviate from the mean radial value by more than 10 units are removed.

14. A method according to claim 1, further comprising applying quadratic regression to the remaining boundary values to construct the second boundary.

15. A method according to claim 1, further comprising defining the second boundary in Cartesian coordinates, prior to identifying the pixels in (iv).

16. A method according to claim 1, wherein constructing the modified retina fundus image comprises:
   copying the identified pixels into the second boundary; and
   filling unoccupied pixels within the second boundary with a background of the modified retina fundus image.

17. A method according to claim 1, further comprising rescaling the modified retina fundus image to 512×512 pixels.

18. A non-transient computer readable medium storing executable instructions that, when executed by a processor, causes the processor to perform the method of claim 1.

19. A deep learning system for screening eye diseases, the deep learning system including a dataset trained by the retina fundus image of claim 1.

* * * * *